(12) United States Patent
Kubiak et al.

(10) Patent No.: US 9,427,309 B2
(45) Date of Patent: Aug. 30, 2016

(54) SOFT TISSUE REPAIR DEVICES, SYSTEMS, AND METHODS

(71) Applicant: CONEXTIONS, INC., Salt Lake City, UT (US)

(72) Inventors: Erik N. Kubiak, Salt Lake City, UT (US); Shawn P. Reese, Salt Lake City, UT (US)

(73) Assignee: CoNextions, Inc., Sandy, UT (US)

( * ) Notice: Subject to any disclaimer, the term of this patent is extended or adjusted under 35 U.S.C. 154(b) by 0 days.

(21) Appl. No.: 13/953,709

(22) Filed: Jul. 29, 2013

(65) Prior Publication Data

US 2014/0067061 A1  Mar. 6, 2014

Related U.S. Application Data

(60) Provisional application No. 61/677,239, filed on Jul. 30, 2012, provisional application No. 61/804,570, filed on Mar. 22, 2013.

(51) Int. Cl.
| | |
|---|---|
| *A61F 2/08* | (2006.01) |
| *A61B 17/064* | (2006.01) |
| *A61B 17/11* | (2006.01) |
| *A61B 17/08* | (2006.01) |
| *A61B 17/04* | (2006.01) |
| *A61B 17/00* | (2006.01) |

(52) U.S. Cl.
CPC ............ *A61F 2/0811* (2013.01); *A61B 17/064* (2013.01); *A61B 17/08* (2013.01); *A61B 17/1146* (2013.01); *A61B 17/0487* (2013.01); *A61B 2017/00867* (2013.01); *A61B 2017/0496* (2013.01); *A61B 2017/1103* (2013.01); *A61B 2017/1132* (2013.01)

(58) Field of Classification Search
CPC .................. A61B 17/1146; A61F 2002/0847; A61F 2002/0864
See application file for complete search history.

(56) References Cited

U.S. PATENT DOCUMENTS

| | | |
|---|---|---|
| 3,166,072 A | 1/1965 | Sullivan et al. |
| 4,388,926 A | 6/1983 | Shalaby et al. |
| 4,414,967 A | 11/1983 | Shapiro |
| 4,461,298 A | 7/1984 | Shalaby et al. |

(Continued)

OTHER PUBLICATIONS

International Search Report dated Oct. 10, 2013 for International Application No. PCT/US2013/052735 (7 pages).

(Continued)

*Primary Examiner* — Thomas J Sweet
*Assistant Examiner* — Daniel Bissing
(74) *Attorney, Agent, or Firm* — David L. Stott

(57) ABSTRACT

Devices, systems and/or methods for repairing soft tissue, such as, a lacerated tendon. A repair device includes a frame having a tubular structure with a longitudinal length and struts at least partially defining the tubular structure. The frame includes a first portion and a second portion with an intermediate portion therebetween, each extending along the longitudinal length. The intermediate portion is configured to substantially maintain a fixed position and is configured to be positioned over first and second ends of the lacerated tendon to substantially maintain the first end abutted against the second end. The first portion and the second portion of the frame are configured to be positioned over separate portions of the tendon and configured to move and elongate along a length of the respective first portion and second portion of the frame as the portions of the tendon elongate.

19 Claims, 9 Drawing Sheets

(56) References Cited

U.S. PATENT DOCUMENTS

| | | | |
|---|---|---|---|
| 4,469,101 | A | 9/1984 | Coleman et al. |
| 4,489,875 | A | 12/1984 | Crawford et al. |
| 4,548,202 | A | 10/1985 | Duncan |
| 4,610,250 | A | 9/1986 | Green |
| 4,655,980 | A | 4/1987 | Chu |
| 4,776,890 | A | 10/1988 | Chu |
| 4,810,549 | A | 3/1989 | Abrams et al. |
| 4,873,976 | A | 10/1989 | Schreiber |
| 4,942,875 | A | 7/1990 | Hlavacek et al. |
| 4,946,467 | A | 8/1990 | Ohi et al. |
| 4,960,420 | A | 10/1990 | Goble et al. |
| 4,983,184 | A | 1/1991 | Steinemann |
| 5,047,103 | A | 9/1991 | Abrams et al. |
| 5,061,283 | A | 10/1991 | Silvestrini |
| 5,163,956 | A | 11/1992 | Liu et al. |
| 5,207,851 | A | 5/1993 | Abrams |
| 5,250,049 | A | 10/1993 | Michael |
| 5,290,552 | A | 3/1994 | Sierra et al. |
| 5,292,334 | A | 3/1994 | Howansky |
| 5,306,500 | A | 4/1994 | Rhee et al. |
| 5,312,023 | A | 5/1994 | Green et al. |
| 5,326,013 | A | 7/1994 | Green et al. |
| 5,329,943 | A | 7/1994 | Johnson |
| 5,342,376 | A | 8/1994 | Ruff |
| 5,346,746 | A | 9/1994 | Abrams |
| 5,413,791 | A | 5/1995 | Rhee et al. |
| 5,446,091 | A | 8/1995 | Rhee et al. |
| 5,447,265 | A | 9/1995 | Vidal et al. |
| 5,458,636 | A | 10/1995 | Brancato |
| 5,465,894 | A | 11/1995 | Clark et al. |
| 5,480,644 | A | 1/1996 | Freed |
| 5,510,418 | A | 4/1996 | Rhee et al. |
| 5,523,348 | A | 6/1996 | Rhee et al. |
| 5,527,341 | A | 6/1996 | Gogolewski et al. |
| 5,542,594 | A | 8/1996 | McKean et al. |
| 5,575,803 | A | 11/1996 | Cooper et al. |
| 5,580,923 | A | 12/1996 | Yeung et al. |
| 5,597,637 | A | 1/1997 | Abrams et al. |
| 5,603,443 | A | 2/1997 | Clark et al. |
| 5,607,094 | A | 3/1997 | Clark et al. |
| 5,630,842 | A | 5/1997 | Brodniewicz |
| 5,667,839 | A | 9/1997 | Berg |
| 5,711,472 | A | 1/1998 | Bryan |
| 5,716,981 | A | 2/1998 | Hunter et al. |
| 5,723,008 | A | 3/1998 | Gordon |
| 5,728,110 | A | 3/1998 | Vidal et al. |
| 5,732,871 | A | 3/1998 | Clark et al. |
| 5,756,678 | A | 5/1998 | Shenoy et al. |
| 5,766,250 | A | 6/1998 | Chervitz et al. |
| 5,800,544 | A | 9/1998 | Demopulos et al. |
| 5,807,581 | A | 9/1998 | Rosenblatt et al. |
| 5,858,156 | A | 1/1999 | Abrams et al. |
| 5,860,229 | A | 1/1999 | Morgenstern |
| 5,865,361 | A | 2/1999 | Milliman et al. |
| 5,908,427 | A | 6/1999 | McKean et al. |
| 5,916,224 | A | 6/1999 | Esplin |
| 5,961,520 | A | 10/1999 | Beck, Jr. et al. |
| 5,964,774 | A | 10/1999 | McKean et al. |
| 5,980,524 | A | 11/1999 | Justin et al. |
| 5,997,811 | A | 12/1999 | Esposito |
| 6,010,764 | A | 1/2000 | Abrams |
| 6,030,410 | A | 2/2000 | Zurbrugg |
| 6,045,560 | A | 4/2000 | McKean et al. |
| 6,079,606 | A | 6/2000 | Milliman et al. |
| 6,080,192 | A | 6/2000 | Demopulos et al. |
| 6,083,332 | A | 7/2000 | Abrams |
| 6,086,547 | A | 7/2000 | Hanssen et al. |
| 6,099,538 | A | 8/2000 | Moses et al. |
| 6,106,556 | A | 8/2000 | Demopulos et al. |
| 6,110,560 | A | 8/2000 | Abrams |
| 6,111,165 | A | 8/2000 | Berg |
| 6,241,139 | B1 | 6/2001 | Milliman et al. |
| 6,241,747 | B1 | 6/2001 | Ruff |
| 6,277,394 | B1 | 8/2001 | Sierra |
| 6,330,965 | B1 | 12/2001 | Milliman et al. |
| 6,333,347 | B1 | 12/2001 | Hunter et al. |
| 6,358,557 | B1 | 3/2002 | Wang et al. |
| 6,383,199 | B2 | 5/2002 | Carter et al. |
| 6,413,742 | B1 | 7/2002 | Olsen et al. |
| D462,766 | S | 9/2002 | Jacobs et al. |
| 6,472,171 | B1 | 10/2002 | Toman et al. |
| 6,485,503 | B2 | 11/2002 | Jacobs et al. |
| 6,495,127 | B1 | 12/2002 | Wallace et al. |
| 6,515,016 | B2 | 2/2003 | Hunter |
| 6,551,315 | B2 | 4/2003 | Kortenbach et al. |
| 6,644,532 | B2 | 11/2003 | Green et al. |
| 6,645,226 | B1 | 11/2003 | Jacobs et al. |
| 6,669,073 | B2 | 12/2003 | Milliman et al. |
| 6,689,803 | B2 | 2/2004 | Hunter |
| 6,712,830 | B2 | 3/2004 | Esplin |
| 6,716,226 | B2 | 4/2004 | Sixto, Jr. et al. |
| 6,740,100 | B2 | 5/2004 | Demopulos et al. |
| 6,743,240 | B2 | 6/2004 | Smith et al. |
| 6,773,450 | B2 | 8/2004 | Leung et al. |
| 6,824,548 | B2 | 11/2004 | Smith et al. |
| 6,830,174 | B2 | 12/2004 | Hillstead et al. |
| 6,843,794 | B2 | 1/2005 | Sixto, Jr. et al. |
| 6,877,647 | B2 | 4/2005 | Green et al. |
| 6,893,452 | B2 | 5/2005 | Jacobs |
| 6,945,979 | B2 | 9/2005 | Kortenbach et al. |
| 6,953,138 | B1 | 10/2005 | Dworak et al. |
| 6,953,139 | B2 | 10/2005 | Milliman et al. |
| 6,962,594 | B1 | 11/2005 | Thevenet |
| 6,991,643 | B2 | 1/2006 | Saadat |
| 7,016,194 | B1 | 3/2006 | Wong |
| 7,056,331 | B2 | 6/2006 | Kaplan et al. |
| 7,070,602 | B2 | 7/2006 | Smith et al. |
| 7,090,685 | B2 | 8/2006 | Kortenbach et al. |
| 7,121,446 | B2 | 10/2006 | Arad et al. |
| 7,129,209 | B2 | 10/2006 | Rhee |
| 7,156,862 | B2 | 1/2007 | Jacobs et al. |
| 7,172,615 | B2 | 2/2007 | Morriss et al. |
| 7,176,256 | B2 | 2/2007 | Rhee et al. |
| 7,226,468 | B2 | 6/2007 | Ruff |
| 7,229,413 | B2 | 6/2007 | Violante et al. |
| 7,232,445 | B2 | 6/2007 | Kortenbach et al. |
| 7,296,724 | B2 | 11/2007 | Green et al. |
| 7,303,107 | B2 | 12/2007 | Milliman et al. |
| 7,309,346 | B2 | 12/2007 | Martinek |
| 7,328,829 | B2 | 2/2008 | Arad et al. |
| 7,343,920 | B2 | 3/2008 | Toby et al. |
| 7,354,627 | B2 | 4/2008 | Pedrozo et al. |
| 7,398,907 | B2 | 7/2008 | Racenet et al. |
| 7,401,720 | B1 | 7/2008 | Durrani |
| 7,438,209 | B1 | 10/2008 | Hess et al. |
| 7,464,848 | B2 | 12/2008 | Green et al. |
| 7,510,566 | B2 | 3/2009 | Jacobs et al. |
| 7,530,484 | B1 | 5/2009 | Durrani |
| 7,565,993 | B2 | 7/2009 | Milliman et al. |
| 7,568,604 | B2 | 8/2009 | Ehrenfels et al. |
| 7,600,663 | B2 | 10/2009 | Green |
| 7,604,151 | B2 | 10/2009 | Hess et al. |
| 7,611,038 | B2 | 11/2009 | Racenet et al. |
| 7,611,521 | B2 | 11/2009 | Lubbers et al. |
| 7,615,058 | B2 | 11/2009 | Sixto, Jr. et al. |
| 7,624,487 | B2 | 12/2009 | Trull et al. |
| 7,635,074 | B2 | 12/2009 | Olson et al. |
| 7,640,617 | B2 | 1/2010 | Kennedy et al. |
| 7,641,091 | B2 | 1/2010 | Olson et al. |
| 7,665,646 | B2 | 2/2010 | Prommersberger |
| 7,708,759 | B2 | 5/2010 | Lubbers et al. |
| 7,727,246 | B2 | 6/2010 | Sixto, Jr. et al. |
| 7,727,248 | B2 | 6/2010 | Smith et al. |
| 7,771,468 | B2 | 8/2010 | Whitbourne et al. |
| 7,819,896 | B2 | 10/2010 | Racenet |
| 7,824,426 | B2 | 11/2010 | Racenet et al. |
| 7,828,189 | B2 | 11/2010 | Holsten et al. |
| 7,842,097 | B2 | 11/2010 | Yamamoto et al. |
| 7,845,533 | B2 | 12/2010 | Marczyk et al. |
| 7,861,907 | B2 | 1/2011 | Green et al. |
| 7,891,531 | B1 | 2/2011 | Ward |
| 7,909,224 | B2 | 3/2011 | Prommersberger |
| 7,926,692 | B2 | 4/2011 | Racenet et al. |
| 7,942,304 | B2 | 5/2011 | Taylor et al. |

(56) References Cited

U.S. PATENT DOCUMENTS

| | | |
|---|---|---|
| 7,942,885 B2 | 5/2011 | Sixto, Jr. et al. |
| 7,950,561 B2 | 5/2011 | Aranyi |
| 8,006,700 B2 | 8/2011 | Demopulos et al. |
| 8,008,598 B2 | 8/2011 | Whitman et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,021,378 B2 | 9/2011 | Sixto, Jr. et al. |
| 8,029,563 B2 | 10/2011 | House et al. |
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 8,062,314 B2 | 11/2011 | Sixto, Jr. et al. |
| 8,062,330 B2 | 11/2011 | Prommersberger et al. |
| 8,062,363 B2 | 11/2011 | Hirpara et al. |
| 8,066,721 B2 | 11/2011 | Kortenbach et al. |
| 8,070,033 B2 | 12/2011 | Milliman et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,113,409 B2 | 2/2012 | Cohen et al. |
| 8,114,129 B2 | 2/2012 | Lubbers et al. |
| 8,118,834 B1 | 2/2012 | Goraltchouk et al. |
| 8,123,101 B2 | 2/2012 | Racenet et al. |
| 8,141,762 B2 | 3/2012 | Bedi et al. |
| 8,157,151 B2 | 4/2012 | Ingmanson et al. |
| 8,186,557 B2 | 5/2012 | Cohen et al. |
| 8,186,560 B2 | 5/2012 | Hess et al. |
| 8,205,620 B2 | 6/2012 | Taylor et al. |
| 8,210,414 B2 | 7/2012 | Bettuchi et al. |
| 8,210,416 B2 | 7/2012 | Milliman et al. |
| 8,256,654 B2 | 9/2012 | Bettuchi et al. |
| 8,256,656 B2 | 9/2012 | Milliman et al. |
| 8,292,152 B2 | 10/2012 | Milliman et al. |
| 8,298,286 B2 | 10/2012 | Trieu |
| 8,308,041 B2 | 11/2012 | Kostrzewski |
| 8,308,042 B2 | 11/2012 | Aranyi |
| 8,308,046 B2 | 11/2012 | Prommersberger |
| 8,322,455 B2 | 12/2012 | Shelton, IV et al. |
| 8,328,061 B2 | 12/2012 | Kasvikis |
| 8,342,377 B2 | 1/2013 | Milliman et al. |
| 8,348,129 B2 | 1/2013 | Bedi et al. |
| 8,439,936 B2 | 5/2013 | McClellan |
| 8,453,905 B2 | 6/2013 | Holcomb et al. |
| 8,453,910 B2 | 6/2013 | Bettuchi et al. |
| 8,464,925 B2 | 6/2013 | Hull et al. |
| 8,469,252 B2 | 6/2013 | Holcomb et al. |
| 8,480,692 B2 | 7/2013 | McClellan |
| 8,485,412 B2 | 7/2013 | Shelton, IV et al. |
| 8,540,131 B2 | 9/2013 | Swayze |
| 8,550,325 B2 | 10/2013 | Cohen et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | (Prommersberger) Stopek |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess et al. |
| 8,740,034 B2 | 6/2014 | Morgan et al. |
| 8,801,732 B2 | 8/2014 | Harris et al. |
| 8,840,003 B2 | 9/2014 | Morgan et al. |
| 8,905,287 B2 | 12/2014 | Racenet et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0192280 A1 | 12/2002 | Hunter et al. |
| 2003/0069602 A1 | 4/2003 | Jacobs et al. |
| 2003/0105489 A1 | 6/2003 | Eichhorn et al. |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1* | 1/2004 | Jacobs et al. ............... 606/153 |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1* | 11/2004 | Bonutti ..................... 606/151 |
| 2004/0224023 A1 | 11/2004 | Hunter et al. |
| 2004/0267362 A1 | 12/2004 | Hwang et al. |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0149349 A1 | 7/2006 | Garbe |
| 2006/0240064 A9 | 10/2006 | Hunter et al. |
| 2006/0240113 A1 | 10/2006 | Hunter et al. |
| 2007/0021779 A1 | 1/2007 | Garvin et al. |
| 2007/0026043 A1 | 2/2007 | Guan et al. |
| 2007/0027527 A1* | 2/2007 | Williams ............... A61F 2/91 623/1.15 |
| 2007/0065663 A1 | 3/2007 | Trull et al. |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0234731 A1 | 9/2008 | Leung et al. |
| 2008/0247987 A1 | 10/2008 | Liggins et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0048537 A1 | 2/2009 | Lydon et al. |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0280153 A1 | 11/2009 | Hunter et al. |
| 2009/0324720 A1 | 12/2009 | He et al. |
| 2010/0016872 A1 | 1/2010 | Bayton et al. |
| 2010/0160718 A1 | 6/2010 | Villafana et al. |
| 2010/0217314 A1 | 8/2010 | Holsten et al. |
| 2011/0125287 A1 | 5/2011 | Hotter et al. |
| 2011/0155787 A1 | 6/2011 | Baxter, III et al. |
| 2011/0288565 A1 | 11/2011 | Kubiak et al. |
| 2011/0288566 A1 | 11/2011 | Kubiak |
| 2011/0301706 A1 | 12/2011 | Brooks et al. |
| 2012/0203253 A1 | 8/2012 | Kubiak |
| 2013/0131781 A1* | 5/2013 | Greenhalgh ......... A61B 19/026 623/1.15 |
| 2013/0144310 A1 | 6/2013 | Gordon et al. |

(56) References Cited

U.S. PATENT DOCUMENTS

2014/0039551 A1  2/2014  Donahue
2015/0272567 A1  10/2015  Feezor et al.

OTHER PUBLICATIONS

Momose, et al., "Suture Techniques With High Breaking Strength and Low Gliding Resistance: Experiments in the Dog Flexor Digitorum Profundus Tendon," Acta Orthop Scan, 2001, 72(6):635-641.

Chunfeng, et al., "Enhancing the Strength of the Tendon-Suture Interface Using 1-Ethyl-3-(3-dimethylaminoproply) Carbodimide Hydrochloride and Cyanoacrylate," Journal of Hand Surgery, 2007, 32(5): 606-11.

Burkhead, et al., "Use of Graft Jacket As an Augmentation for Massive Rotator Cuff Tears," Semin Arthro, 2007, 18 (1): 11-18.

McKenzie, "An Experimental Multiple Barbed Suture for the Long Flexor Tensons of the Palm and Fingers," Journal of Bone and Joint Surgery, Aug. 1967, pp. 440-447, vol. 49 B, No. 3.

Leung, et al., "Barbed, Bi-Directional Medical Sutures: Biomechanical Properties and Wound Closure Efficacy Study," Society for Biomaterials 28th Annual Meeting Transactions, 2002, p. 724.

Hirpara et al., "A Barbed Device for Digital Flexor Tendon Repair," http://proceedings.jbjs.org.uk/cgi/content/absract/92-B/SUPP_11/291-d, Mar. 2010.

International Search Report dated Jul. 20, 2015 for International Application No. PCT/US2015/020231 (10 pages).

\* cited by examiner

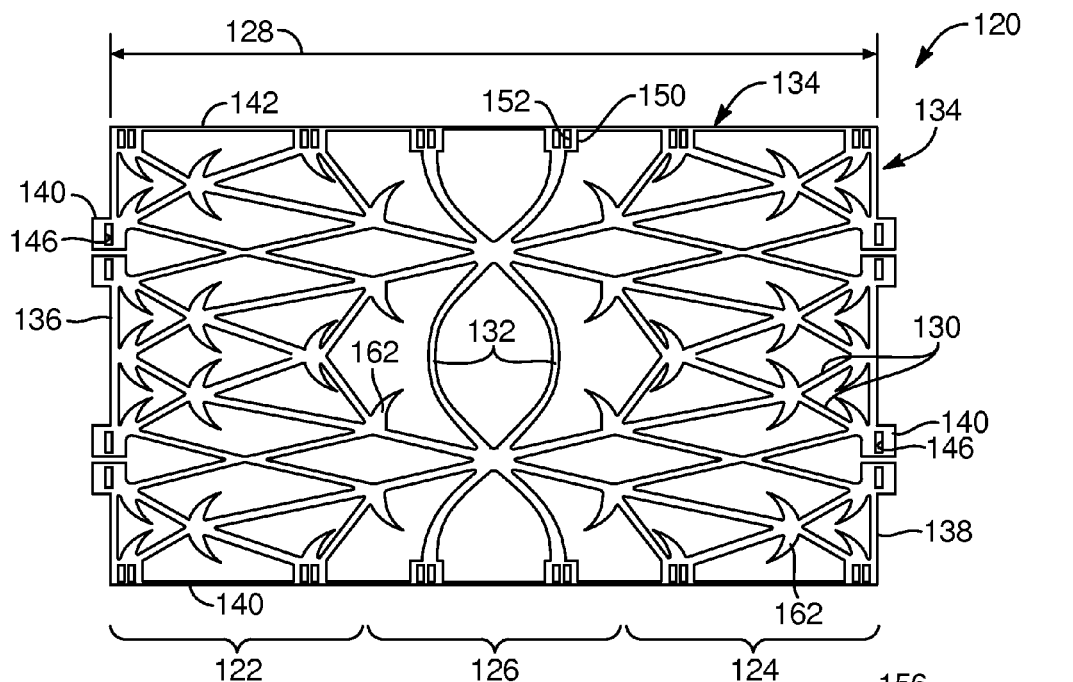
FIG. 7
FIG. 7A
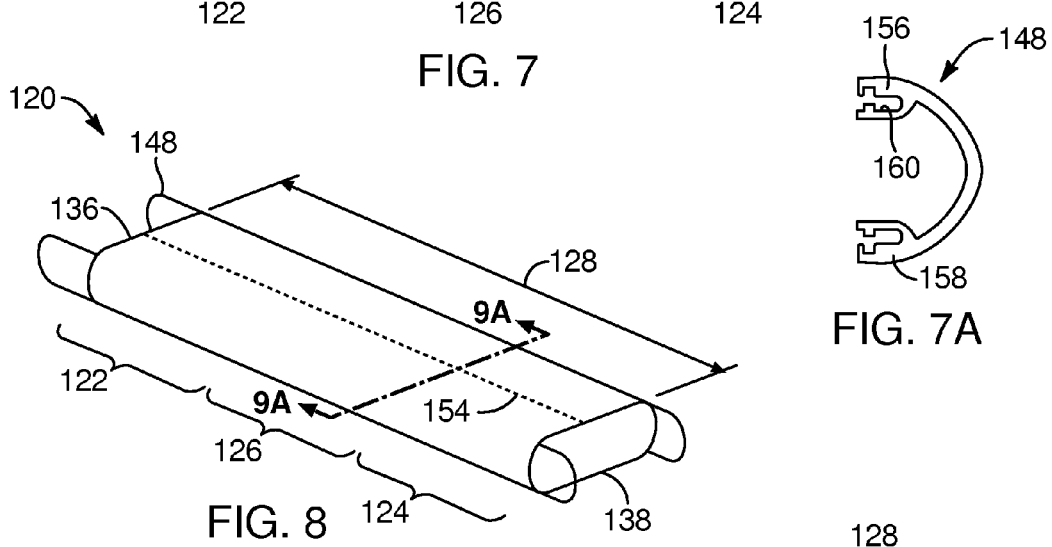
FIG. 8
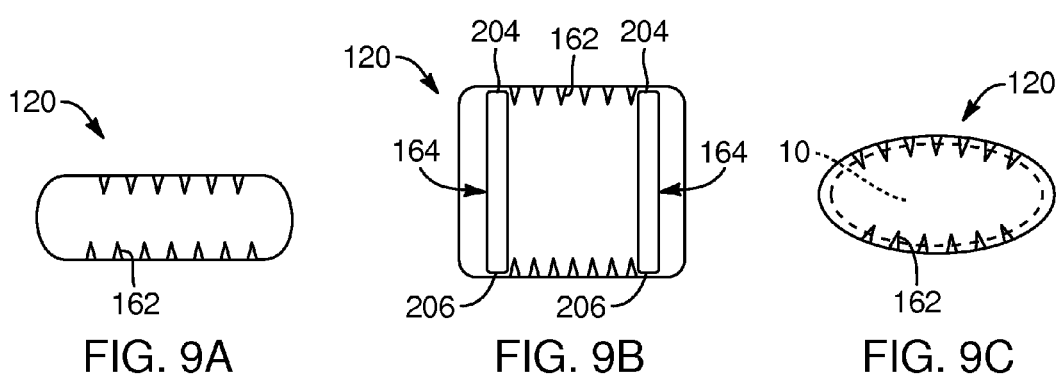
FIG. 9A    FIG. 9B    FIG. 9C

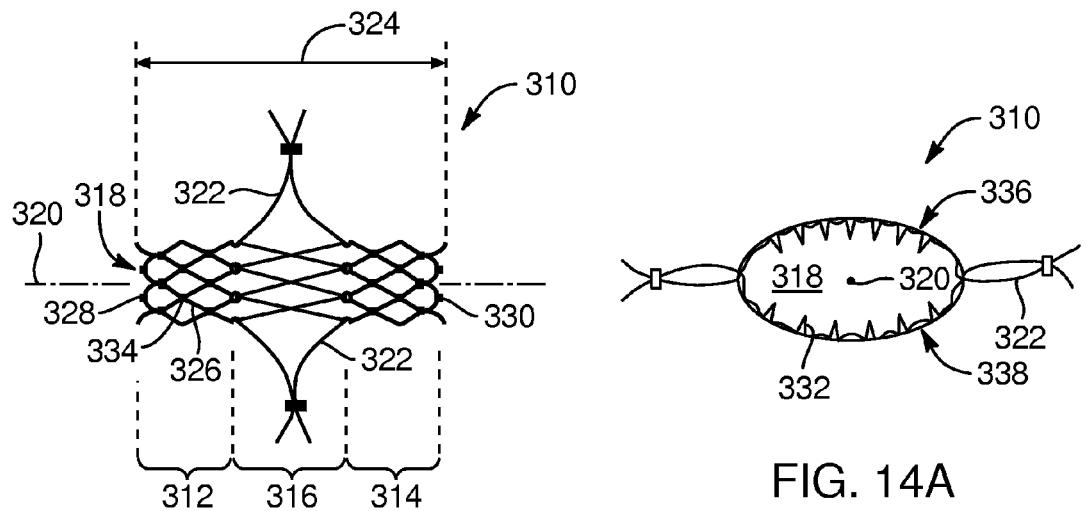
FIG. 14
FIG. 14A
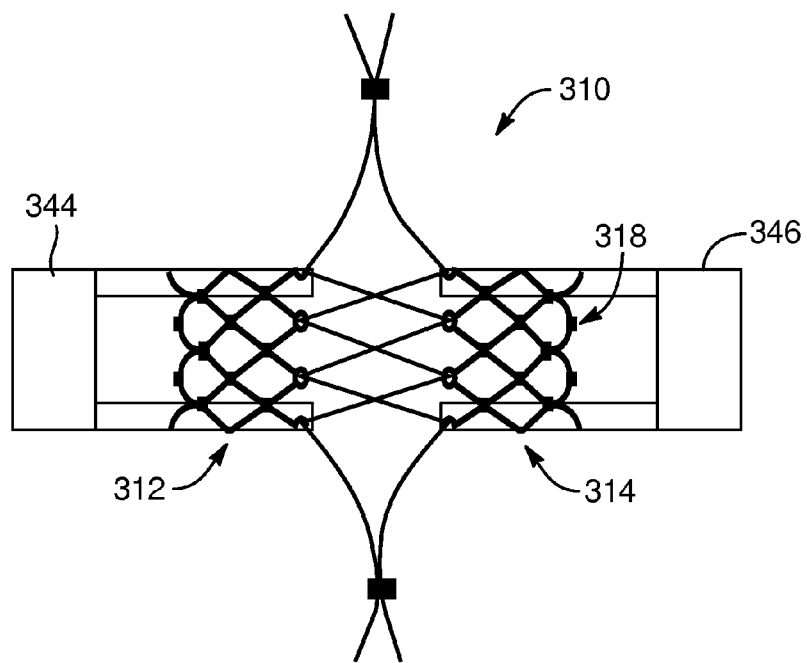
FIG. 15

SOFT TISSUE REPAIR DEVICES, SYSTEMS, AND METHODS

CROSS-REFERENCE TO RELATED APPLICATIONS

The present application claims the benefit of U.S. Provisional Application No. 61/677,239, filed on Jul. 30, 2012, and U.S. Provisional Application No. 61/804,570, filed on Mar. 22, 2013, the contents of which are hereby incorporated by reference in their entirety.

TECHNICAL FIELD

The present invention relates generally to soft tissue repair. More particularly, the present invention relates to devices, systems, and methods for repairing lacerated tendons.

BACKGROUND

Lacerated flexor tendon repair, as an example, is a procedure performed approximately 145,000 times a year in the United States alone. For all types of tendons in the human anatomy, early post-operative mobilization is beneficial to restoring maximal tendon function following injury and repair. Adhesion formation is a common complication following tendon repair, but can be reduced through motion rehabilitation programs. By preventing adhesion formation and gliding resistance, tendon healing may be enhanced. However, the failure rate of tendon repairs is close to 30 percent, primarily because of overloading at the repair site. Although an objective of tendon repair is to provide adequate strength for passive and active motion during rehabilitation, it is important to maintain a delicate balance between rehabilitative motion protocols and fatiguing the repair site.

A procedure for lacerated tendon repair is to use suture to mend the two ends of a tendon together using complex suture patterns. While this provides a good initial repair, the strength and quality of the repair may quickly degrade with subsequent loading and mobilization. Although postoperative therapy may be utilized to reduce adhesion, the resulting tension can induce gap formation or tendon rupture at the repair site, seriously impairing the outcome of the repair. Gapping at the repair site has many negative effects, such as reduced repair strength, tendon rupture, and an increased probability for adhesion.

BRIEF SUMMARY OF THE INVENTION

Embodiments of the present invention are directed to various devices, systems and methods for repairing soft tissue in a body. For example, in one embodiment, a soft tissue repair device is provided configured to fuse a first tendon end and a second tendon end of a lacerated tendon together. The soft tissue repair device includes a frame having a tubular structure that defines an axis and a bore. The frame includes multiple struts to at least partially define the tubular structure and is configured to receive the first tendon end and the second tendon end. The frame includes a first portion and a second portion with an intermediate portion therebetween. The intermediate portion is configured to be positioned over the first and second tendon ends to substantially maintain the first tendon end to abut the second tendon end. Further, the intermediate portion is configured to substantially resist elongation so as to maintain a substantially fixed position relative to the first and second tendon ends. The first portion and the second portion are configured to be positioned over separate portions of the tendon such that the frame is configured to elongate along a length of the respective first portion and the second portion of the frame as the portions of the tendon elongate.

In one embodiment, the frame includes pad portions defining holes therethrough such that the pad portions are configured to receive staples through the holes to secure the frame to the tendon. In another embodiment, the frame is secured to the tendon with staples. In another embodiment, the frame includes multiple tines extending from the first portion and the second portion of the frame to engage and anchor to the tendon.

In another embodiment, the intermediate portion includes a wire connecting the first portion and the second portion of the frame together. In another embodiment, the frame is configured to substantially maintain the fixed position along a length of the intermediate portion of the frame.

In still another embodiment, the struts of the first portion and the second portion of the frame are moveable to an arcuate position. In another embodiment, the struts of the first portion and the second portion of the frame are moveable to an arcuate position with the struts of the intermediate portion substantially maintaining the fixed position. In another embodiment, the struts of the first portion and the second portion include a multi-cellular structure.

In yet another embodiment, the frame includes a first side, a second side, an upper side and a lower side, the first side being opposite the second side, the first and second sides including the struts to at least partially define the first and second sides, the struts extending to multiple pad portions to at least partially define the upper and lower sides of the frame, each pad portion along the upper side being directly opposite and facing another pad portion along the lower side of the frame. In another embodiment, the pad portions comprise holes extending therethrough configured to receive staples for securing the first portion and the second portion of the frame to the tendon.

In accordance with another embodiment of the present invention, a repair device configured to fuse tissue at a repair site is provided. The repair device includes a frame having multiple struts, the frame including a moveable portion and a stabilizing portion. The moveable portion is coupled to the stabilizing portion. The stabilizing portion of the frame extends over the repair site and the moveable portion of the frame is configured to be anchored to a portion of tissue separate from the repair site. With this arrangement, the moveable portion of the frame is moveable to elongate along a length of the moveable portion of the frame as the portion of tissue elongates with a load placed thereon and the stabilizing portion of the frame maintains a substantially fixed position over the repair site.

In one embodiment, the moveable portion of the frame includes pad portions defining holes therethrough such that the pad portions are configured to receive staples through the holes to secure the frame to the tendon. In another embodiment, the frame is secured to the tendon with staples. In another embodiment, the frame includes multiple tines extending from the moveable portion of the frame for securing the frame to the tendon.

In another embodiment, the moveable portion of the frame is moveable to an arcuate position. In another embodiment, the moveable portion of the frame is moveable to an arcuate position as the portion of tissue to which the moveable portion is anchored moves to an arcuate position.

In still another embodiment, the stabilizing portion comprises a wire. Further, in another embodiment, the struts of the frame comprise a multi-cellular structure.

In accordance with another embodiment of the present invention, a method of repairing a lacerated tendon having a first tendon end and a second tendon end. The method includes the steps of providing a frame having a longitudinal length and having a tubular structure defining an axis and a bore, the frame including multiple struts to at least partially define the tubular structure, and the frame including a first portion and a second portion with an intermediate portion therebetween; inserting the first tendon end into the first portion of the frame so that the first tendon end is positioned within the intermediate portion of the frame; inserting the second tendon end into the second portion of the frame so that the second tendon end is positioned within the intermediate portion of the frame and adjacent the first tendon end; and anchoring the first portion and the second portion of the frame to the tendon; wherein the intermediate portion is configured to be positioned over the first and second tendon ends of the tendon to substantially maintain the first tendon end abutted against the second tendon end such that the frame is configured to maintain a fixed position along a length of the intermediate portion of the frame; and wherein the frame is configured to elongate along a length of the respective first portion and the second portion of the frame as portions of the tendon elongate with a load being placed on the tendon.

In one embodiment, the method step of anchoring includes anchoring the first portion and the second portion of the frame to the tendon with staples. In another embodiment, the method step of anchoring includes anchoring the first portion and the second portion of the frame to the tendon with tines extending from the respective first portion and second portion of the frame. In still another embodiment, the method step of providing includes providing the first portion and the second portion of the frame to be moveable to an arcuate position as the tendon moves to a tendon arcuate position.

In accordance with another embodiment of the present invention, a soft tissue repair device is provided configured to fuse a first tendon end and a second tendon end of a lacerated tendon together. The repair device includes a frame having struts defining a multi-cellular structure along a length of the frame. The frame includes a first portion and a second portion with an intermediate portion therebetween. The intermediate portion is configured to be positioned over the first and second tendon ends of the tendon to substantially maintain the first tendon end abutted against the second tendon end. The first portion and the second portion are configured to be positioned over separate portions of the tendon and configured to move and elongate along the length of the frame as the portions of the tendon elongate.

In another embodiment, the first and second portions of the frame include tines that extend therefrom such that the tines are configured to engage the tendon. In another embodiment, the intermediate portion of the frame is configured to be positioned at least on opposing sides of the tendon. Further, in another embodiment, the first portion of the frame and the second portion of the frame are each configured to be positioned at least on opposing sides of the tendon.

In another embodiment, the frame includes an upper frame portion and a lower frame portion, the upper frame portion and the lower frame portion are each configured to extend with a substantially flat configuration and are substantially parallel relative to each other. The upper frame portion and the lower frame portion are coupled together with side frame portions.

In still another embodiment, the frame includes a cross-sectional periphery having a rectangular configuration. In yet another embodiment, the frame includes a cross-sectional periphery having an oval configuration.

In another embodiment, the frame is moveable from a first non-engaging position toward a second engaging position. The first non-engaging position includes a cross-sectional periphery larger than the second engaging position. Further, in one embodiment, the frame includes at least one of a super-elastic material and a steel material.

In accordance with another embodiment of the present invention, a method is provided of repairing a lacerated tendon having a first tendon end and a second tendon end. The method includes providing a frame having struts defining a multi-cellular structure along a length of the frame, the frame including a first portion and a second portion with an intermediate portion therebetween each extending along the length of the frame, the frame moveable between a first position and a second position; positioning the frame over the first tendon end and the second tendon end such that the intermediate portion of the frame is disposed over the first tendon end abutting the second tendon end; moving the frame from the first position to the second position; engaging the tendon with tines extending from the first portion and the second portion of the frame by moving the frame from the first position to the second position; and maintaining the first tendon end abutted to the second tendon end with the intermediate portion of the frame being substantially non-elongatable while the first portion and the second portion of the frame is elongatable along the length thereof so as to facilitate the tendon to elongate with the frame attached thereto.

In another embodiment, the method step of positioning includes positioning the first tendon end and the second tendon end within the frame with a suture. In another embodiment, the method step of moving includes engaging the tendon with tines extending from the first portion and the second portion of the frame. In yet another embodiment, the method step of engaging includes engaging the tendon with tines oriented to extend at an acute angle relative to the length of the frame.

In a further embodiment, the method step of maintaining the first tendon end abutted to the second tendon end includes providing the intermediate portion of the frame with structure that substantially prevents elongation along the length of the frame.

In another embodiment, the method step of moving the frame includes crimping portions of the frame to move and maintain the frame in the second position. In still another embodiment, the method includes positioning an applicator on the frame to hold the frame in the first position to facilitate the positioning the frame over the first tendon end and the second tendon end. In a further embodiment, the method step of moving the frame includes removing the applicator from the frame so that the frame automatically moves from the first position to the second position.

In accordance with another embodiment of the present invention, a soft tissue repair device configured to fuse a first tendon end to a second tendon end of a lacerated tendon is provided. The repair device includes a tubular frame including multiple interconnecting struts defining a multi-cellular tubular configuration. The tubular frame defines an axis and a longitudinal length extending along the axis. The tubular frame is configured to receive the lacerated tendon therein with the first tendon end insertable within a first open end defined in the tubular frame and with the second tendon end insertable within a second open end defined in the tubular frame so that the tubular frame surrounds the lacerated tendon. The frame includes a first portion, a second portion, and an intermediate portion. The first portion and the second portion each extending along the longitudinal length and are configured to elongate along the longitudinal length so that as the tendon naturally elongates the first and second portions of the tubular frame also elongate with the tendon. The intermediate portion extends along the longitudinal length and extends between the first portion and the second portion of the frame. The intermediate portion is configured to substantially resist elongation along the longitudinal length so as to maintain the first tendon end abutted against the second tendon end within the tubular frame.

In one embodiment, the tubular frame includes a cross-section with an oval configuration. In another embodiment, the tubular frame includes at least one of a super-elastic material and a steel material.

In another embodiment, the struts of the intermediate portion extend substantially parallel with the axis of the tubular frame. In another embodiment, the struts of the first portion and the second portion of the tubular frame extend at an acute angle relative to the axis of the frame. In still another embodiment, the struts of the first portion and the second portion of the tubular frame extend at a greater acute angle relative to the axis of the frame than the struts of the intermediate portion extend relative to the axis of the frame. In yet another embodiment, the struts of the first portion and the second portion include a tapered portion so as to facilitate the struts to flex and the first and second portions of the frame to elongate along the length of the frame. In another embodiment, the struts of the first portion and the second portion of the frame include a smaller width than the struts of the intermediate portion of the frame.

In another embodiment, the tubular frame includes a first end and a second end, the first end being opposite the second end, and the first and second ends each including at least one crimp coupled thereto. Such a tubular frame may include a super-elastic material and the crimp may include a steel material.

In accordance with another embodiment of the present invention, a soft tissue repair device configured to maintain a first end and a second end of a lacerated tendon adjacent each other is provided. The soft tissue repair device includes a frame having struts defining a multi-cellular structure and extending along a longitudinal length of the frame. The frame also includes an upper frame portion, a lower frame portion, a first side portion, and a second side portion. The upper frame portion includes an upper first portion and an upper second portion with an upper intermediate portion therebetween. The lower frame portion includes a lower first portion and a lower second portion with a lower intermediate portion therebetween. The first side portion and the second side portion each includes multiple side crimps, the upper frame portion and the lower frame portion coupled together with the side crimps. With this arrangement, the upper frame portion and the lower frame portion with the side crimps coupled thereto are configured to cage or surround the lacerated tendon with the first tendon end and the second tendon end being positioned between the upper intermediate portion and the lower intermediate portion of the frame. Further, the upper and lower intermediate portions are configured to substantially resist elongation to substantially maintain the first tendon end abutted against the second tendon end, and the upper first and second portions and the lower first and second portions of the frame are configured to engage the tendon and configured to elongate along the longitudinal length of the frame so as to facilitate the tendon to naturally elongate with the frame engaged to the tendon.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 7 is a top view of a repair device prior to being formed into a tubular configuration, according to another embodiment of the present invention;

FIG. 7A is a side view of an end crimp, according to another embodiment of the present invention;

FIG. 8 is a simplistic perspective view of the repair device of FIG. 7, depicting the repair device formed into a tubular configuration with end crimps at the ends of the repair device, according to another embodiment of the present invention;

FIG. 9A is a cross-sectional view of the repair device taken from section 9A of FIG. 9, according to an embodiment of the present invention;

FIG. 9B is the sectional view of the repair device shown in FIG. 9A, depicting an applicator expanding the repair device, according to another embodiment of the present invention;

FIG. 9C is the sectional view of the repair device shown in FIG. 9A, depicting the applicator removed and conforming to a tendon positioned within the repair device, according to another embodiment of the present invention;

FIG. 14 is a top view of another embodiment of a repair device, according to the present invention;

FIG. 14A is a side view of the repair device of FIG. 14, according to another embodiment of the present invention;

FIG. 15 is a top view of the repair device, depicting first and second applicators inserted into opposite ends of the repair device, according to another embodiment of the present invention;

DETAILED DESCRIPTION OF THE INVENTION

Figure 1:
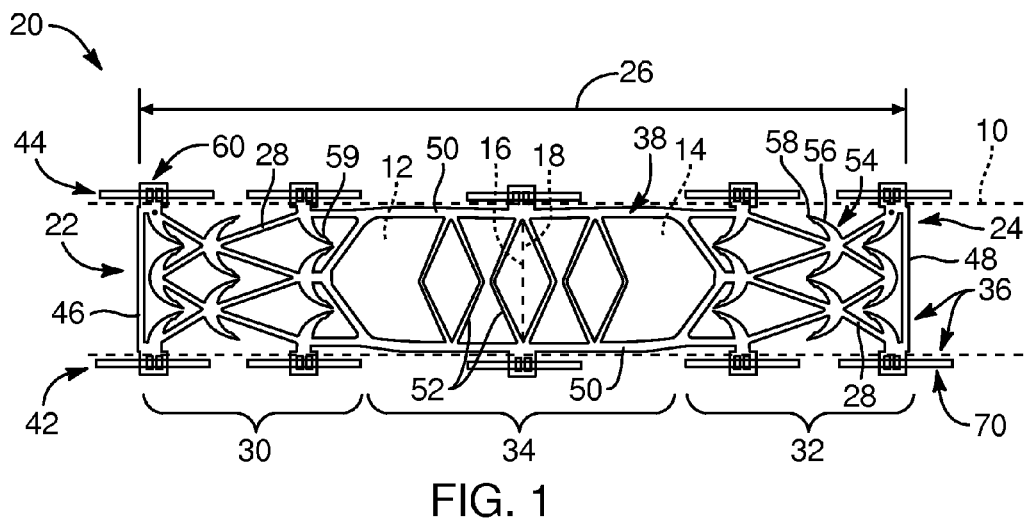
FIG. 1 is a top view of a repair device, depicting a tendon positioned within the repair device, according to an embodiment of the present invention.
Figure 2:
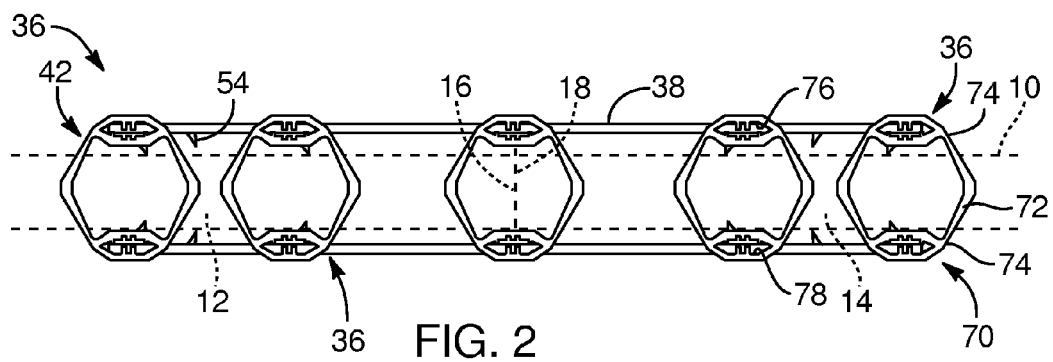
FIG. 2 is a side view of the repair device shown in FIG. 1, according the present invention.
Figure 3:
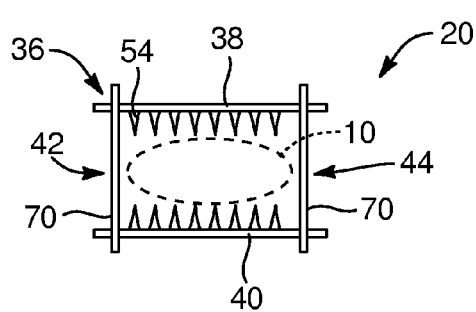
FIG. 3 is an end view of the repair device shown in FIG. 1, depicting the device in a non-engaging first position relative to the tendon, according to one embodiment of the present invention.
Figure 4:
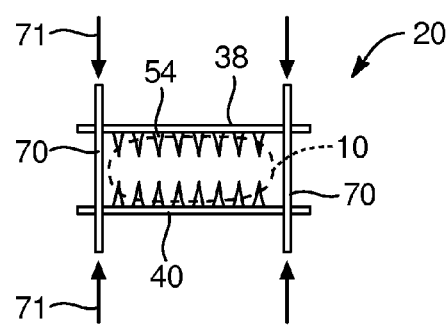
FIG. 4 is an end view of the repair device, depicting the device in an engaging second position relative to the tendon, according to another embodiment of the present invention.

Referring to FIGS. 1-3, a soft tissue repair device 20 is depicted. Such a repair device 20 may be sized and configured to approximate and fuse, for example, a lacerated tendon 10 together. The tendon 10, shown in outline form, may be positioned in the repair device 20 such that a first tendon portion 12 and a second tendon portion 14 with respective first and second tendon ends 16, 18 are abutted against each other. The repair device 20 may include a tubular configuration with opposing first and second open ends 22, 24 to facilitate insertion of the first and second tendon portions 12, 14 therein such that the first and second tendon ends 16, 18 are positioned at about a mid-point of the repair device 20. The repair device 20 may then be moved from a first, non-engaging position to a second, engaging position (FIG. 4).

The repair device 20 may be elongated with a longitudinal length 26 to exhibit the tubular configuration formed from multiple interconnecting struts 28 to define a multi-cellular structure. The struts 28 of the repair device 20 may include structural characteristics that facilitate and resist elongation along portions of the length 26 of the repair device 20. For example, the repair device 20 may include a first portion 30 and a second portion 32 with an intermediate portion 34 therebetween, each extending along the longitudinal length 28 of the repair device 20. The intermediate portion 34 may be configured to substantially resist elongation so that the first and second tendon ends 16, 18 positioned adjacent the intermediate portion 34 maintain their abutted relationship. The first and second portions 30, 32 of the repair device 20 may be configured to engage the tendon 10 and elongate as the tendon elongates to facilitate functionality and a load placed upon the tendon 10. Such elongation of the first and second portions 30, 32 and resistance to elongate at the intermediate portion 34 also substantially prevents overloading and, thus, gapping of the tendon 10 at the repair site.

The repair device 20 may include a frame structure 36. The frame structure 36 may include an upper frame portion 38, a lower frame portion 40, a first side portion 42, and a second side portion 44, each of which portions may be coupled together to form the tubular configuration with a cross-section having a square or rectangular configuration. The upper frame portion 38 and the lower frame portion 40 may be substantially similar in structure as well as the first and second side portions 42, 44 may be substantially similar in structure. Further, the upper frame portion 38 and the lower frame portion 40 may be formed from a variety of metallic materials, such as stainless steel or various alloys, but preferably a super elastic material, such as Nitinol, to provide the desired structural strain characteristics. The first and second side portions 42, 44 may also be formed from a metallic material, such as stainless steel or Nitinol, or both, discussed hereafter.

With reference to FIG. 1, structural features and characteristics will now be set froth for the upper frame portion 38, which will apply equally to the lower frame portion 40. The upper frame portion 38, similar to the lower frame portion (not shown), may include the before-described first portion 30 and the second portion 32 with the intermediate portion 34 therebetween each extending along the longitudinal length 26 of the upper frame portion 38. The first portion 30 extends along the longitudinal length 26 between the intermediate portion 34 and a first end 46 of the upper frame portion. Likewise, the second portion 32 extends along the longitudinal length 26 between the intermediate portion 34 and a second end 48 of the upper frame portion 38. The intermediate portion 34 may be defined by outer rails 50 extending substantially parallel to each other with intermediate stoppers 52 extending laterally between the outer rails 50. The stoppers 52 may be in the form of laterally extending struts between the outer rails 50.

As previously set forth, the repair device 20 includes multiple interconnecting struts 28 defining a multi-cellular structure. For example, the struts 28 of the first portion 30 and the second portion 32 may extend, for the most part, at various angles relative to the longitudinal length 26 of the upper frame portion 38. Such struts 28 of the first portion 30 and the second portion 32 may be sized and configured to facilitate elongation of the respective first and second portions 30, 32 of the upper frame portion 38 such that the struts 28 may flex. In one embodiment, the elongation of the first and second portions 30, 32 of the upper frame portion 38 may gradually increase toward the first and second ends 46, 48 of the upper frame portion 38, respectively. In another embodiment, the strainability or elongation of the first and second portion 30, 32 may increase toward their respective ends in a gradient type manner. The struts 28 of the first and second portions 30, 32 of the upper frame portion 38 may include a substantially constant width along their respective longitudinal strut lengths. In another embodiment, the struts 28 may include a tapered portion along the longitudinal strut lengths to facilitate elongation along the length 26 of the first and second portions 30, 32 of the upper frame portion 38. In still another embodiment, the struts 26 may include a radius along their respective length having a constant width or a taper to facilitate elongation of the first portion 30 and the second portion 32.

The intermediate portion 34 of the upper frame portion 38 may include struts 28 sized and oriented to substantially prevent elongation along the length of the intermediate portion 34. For example, the struts or the rails along the length of the intermediate portion 34, being substantially parallel, substantially limit the ability of the intermediate portion 34 to elongate. As known to one of ordinary skill in the art, other structural features and characteristics may be employed to substantially limit elongation of the intermediate portion 34 as well. The intermediate stoppers 52 may be sized and configured to substantially prevent trumpeting of the first and second tendon ends 16, 18, or tendon portions adjacent thereto, from extending beyond or outside of a plane of the upper and lower frame portions 38, 40.

With respect to FIGS. 1 and 3, the first and second portions 30, 32 of the upper and lower frame portions 38, 40 may include tines 54. In another embodiment, the intermediate portion 34 may also include tines 54. The tines 54 may be sized and configured to aggressively engage and grab the tendon 10 without damaging the tendon. The tines 54 may include a radius and a tapered portion 56 extending to a point 58. The tines 54 may extend from an end portion of a given strut 28 or a node or juncture between adjacently extending struts 28, the tines 54 extending from the first and second portions 30, 32 of the frame structure 36. The tines 54 of the upper frame portion 38 may extend with an orientation toward the intermediate portion 34 and downward. The tines 54 of the lower frame portion 40 may extend with an orientation toward the intermediate portion 34 and upward. Such orientation may be at an acute angle (see FIG. 2) relative to the planes of the respective upper and lower frame portions 38, 40. Such orientation facilitates ready insertion into the tubular configuration of the repair device 20 as well as enhances grabbing the tendon to prevent migration therefrom once the repair device 20 is moved to the second engaging position (FIG. 4). Further, the tines 54 may be configured to flex slightly so as to a grab the tissue but upon tension being placed on the tendon 10 the tines 54 may slightly move or bend to substantially to portion 416 or first intermediate portion 424 substantially prevents elongation to minimize movement at the ends of the lacerated tendon 403. Further, as in previous embodiments, the first portion 412 mnt, the tines 54 may include one or more barbs 59.

Figure 5:
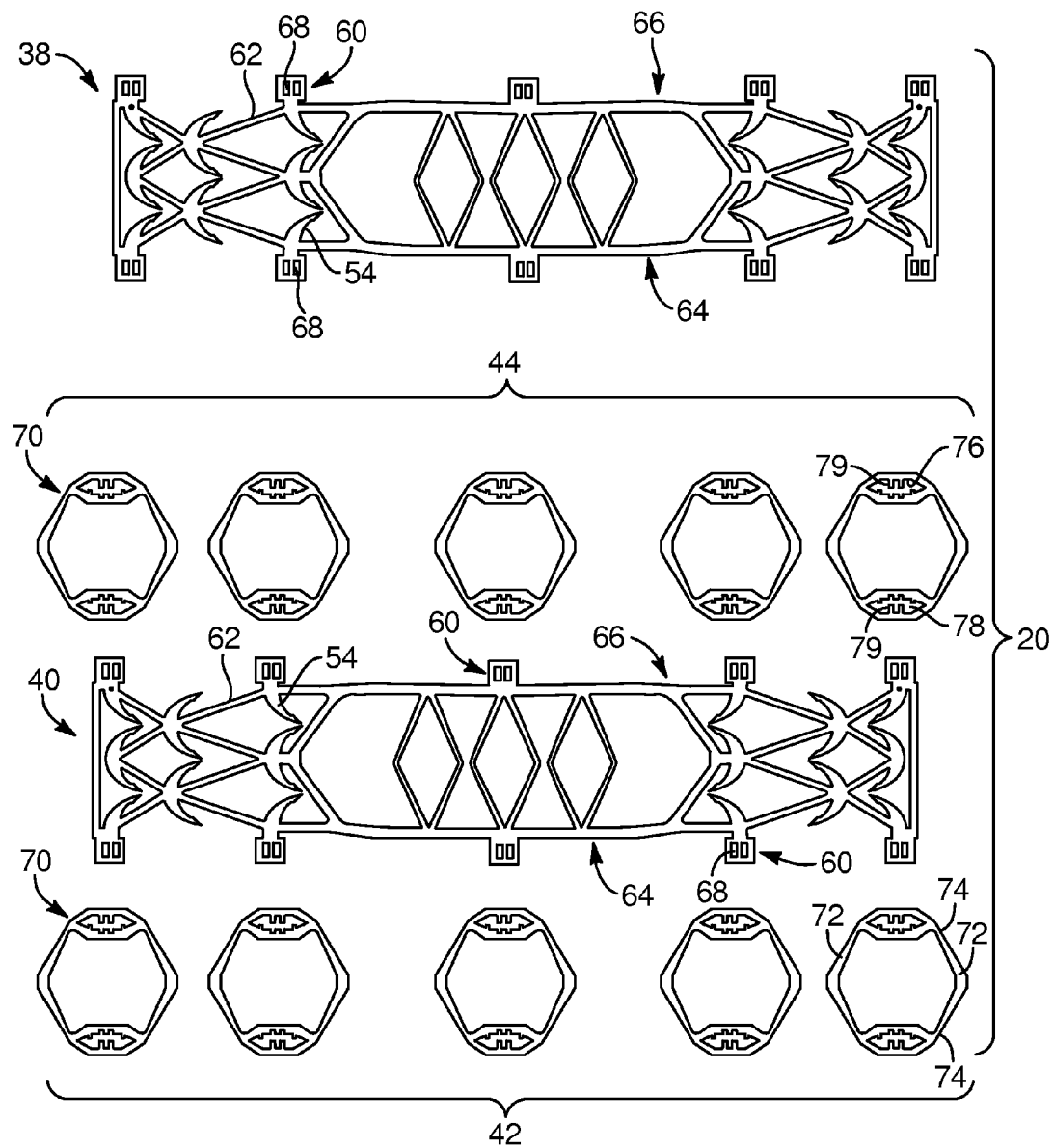
FIG. 5 is an unassembled view of the repair device shown in FIG. 1, depicting various components of a frame including an upper frame portion, a lower frame portion, and side crimps, according to an embodiment of the present invention.

With respect to FIGS. 1, 2 and 5, the upper frame portion 38 and the lower frame portion 40 may include tabs 60. The tabs 60 may extend at or from a periphery 62 of each of the upper and lower frame portions 38, 40. More particularly, the upper frame portion 38 includes a first side 64 and a second side 66 each with at least two tabs 60 (one for each end of the first and second sides 64, 66) and, in this embodiment, five tabs 60 for each of the first and second sides 64, 66. The tabs 60 on the first side 64 correspond and align with the tabs 60 on the second side 66. The tabs 60 for the upper frame portion 38 may correspond and align with the number of tabs 60 for the lower frame portion 40. Each tab 60 may include one or more openings 68 defined therein sized and configured to couple to a side crimp 70.

The first side portion 42 and the second side portion 44 of the repair device 20 may each include at least two side crimps 70 with one at each end to couple to the upper and lower frame portions 38, 40. In this embodiment, the first side portion 42 and the second side portion 44 each includes five side crimps 70. As previously set forth, the side crimps 70 may be sized and configured to couple to the upper and lower frame portions 38, 40. For example, each side crimp 70 may include a closed periphery with side arm portions 72 sized and configured to buckle under a defined force. The side arm portions 72 may include one or more weak portions 74 so as to facilitate the side crimps 70 to deform or buckle upon a force being placed thereto. The side crimps 70 may define an upper opening 76 and a lower opening 78 with structure, such as, teeth 79 that extend in the openings sized and configured to latch or couple to the tabs 60 of the upper and lower frame portions 38, 40, respectively. In other words, the teeth 79 defining a portion of the upper opening 76 of one side crimp 70 may be sized to couple to one of the tabs 60 of the upper frame portion 38. Likewise, the structure or teeth 79 defining a portion of the lower opening 78 of the one side crimp 70 may be sized to couple to one of the tabs 60 of the lower frame portion 40. With this arrangement, the side crimps 70 couple the upper and lower frame portions 38, 40 to provide a tubular configuration to serve as a cage or box-like structure to position the tendon 10 therethrough. The side crimps 70 may be formed from a metallic material, such as a stainless steel. In another embodiment, the side crimps may be formed from a super-elastic material, such as Nitinol.

The side crimps, as depicted in FIGS. 3 and 4, may serve to facilitate the repair device 20 in maintaining its position at both the first non-engaging position and the second engaging position. In particular, in an embodiment where the side crimps 70 are, for example, stainless steel or the like, the structural characteristics of the side crimps 70 maintain the upper and lower frame portions 38, 40 in the first non-engaging position so that the tendon 10 may be easily positioned within the repair device 20. Once the tendon 10 is appropriately positioned within the repair device 20, a force 71 may be placed upon the repair device 20 to sandwich the tendon 10 within the repair device 20 such that the tines 54 engage the tendon 10. Such force 71 buckles the side crimps 70 at the weak portions (not shown) defined therein to facilitate the upper frame portion 38 to move closer to the lower frame portion 40. Due to the structural characteristics of, for example, stainless steel, the side crimps 70 maintain their buckled position to, thereby, maintain the repair device 20 in the second engaging position.

In another embodiment, as previously set forth, the side crimps 70 or first and second side portions 42, 44 of the repair device 20 may be made from a super-elastic material. In such an embodiment, the first and second side portions 42, 44 (FIG. 1) may be constrained to an expanded position with, for example, applicators (see FIGS. 9B and 12) at each end to maintain the repair device in the first non-engaging position. Once the lacerated tendon 10 is inserted within the repair device 20, the applicators may be removed, after which, the first and second side portions 42, 44 may then move toward a relaxed state such that the repair device 20 moves to the second engaging position. In the second engaging position, the upper and lower frame portions 38, 40 move toward each other such that the tines 54 extending from the upper and lower frame portions 38, 40 engage the tendon 10.

In another embodiment, the first and second side portions 42, 44 (FIG. 1) may be formed with a super-elastic material and a stainless steel material or the like. In this embodiment, side crimps 70 may be employed at both ends of the first and second side portions 42, 44 of the repair device 20 with, for example, struts or crimps between the side crimps 70 at the ends. Such an embodiment may need the applicators to maintain the device 20 in the first non-engaging position. Once the applicators are removed, the super-elastic struts or crimps pull the upper and lower frame portions 38, 40 closer together. A force may then be applied to the ends of the first and second side portions 42, 44 to buckle the stainless steel side crimps 70 at the ends of the repair device 20.

Now referring to FIG. 5, one embodiment of an unassembled repair device 20 is shown. Each of the upper and lower frame portions 38, 40 and the side crimps 70 may be laser cut from a flat sheet of metallic material and, as such, the structural components are substantially flat and planar with a low profile (See FIG. 3). As previously set forth, the upper and lower frame portions 38, 40 may be formed from a super-elastic sheet material, such as Nitinol. The side crimps may be formed from a stainless steel sheet material and/or a super-elastic sheet material. As previously set forth, the tines 54 of the upper and lower frame portions 38, 40 may be oriented out-of-plane relative to the upper and lower frame portions 38, 40 from which they respectively extend. As known by one of skill in the art, such orientation may be employed by heat-setting the tines 54 to a pre-determined orientation. Once the heat setting of the tines 54 is completed, the repair device 20 may be assembled. For example, as set forth above, the lower opening 78 defined in each of the side crimps 70 may be coupled to the tabs 60 of the lower frame portion 40. The upper opening 76 defined in the side crimps 70 may then be coupled to the tabs 60 of the upper frame portion 38, as depicted in FIGS. 1 and 2, to thereby assemble the repair device 20.

Figure 5A:
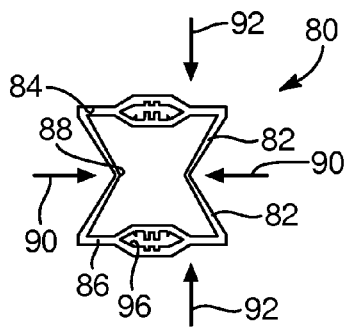
FIG. 5A is another embodiment of a side crimp, according to the present invention.

With respect to FIG. 5A, another embodiment of a side crimp 80 is depicted. In this embodiment, the side crimp 80 may include a closed periphery with arm portions 82 extending between an upper crimp portion 84 and a lower crimp portion 86. The arm portions 82 may include weak portions 88 to facilitate buckling of the side crimp 80, as indicated by arrow 90, upon a force 92 being applied to the side crimp 80. As in the previous side crimp embodiment, the side crimp 80 may include an upper opening 94 and a lower opening 96 defined in the upper crimp portion 84 and lower crimp portion 86, respectively, configured to couple to tabs 60 of the upper and lower frame portions 38, 40. As known by one of ordinary skill in the art, other structural configurations may be employed for the side crimps 80 to facilitate crimping the repair device 20 to the second engaging position.

Figure 6:
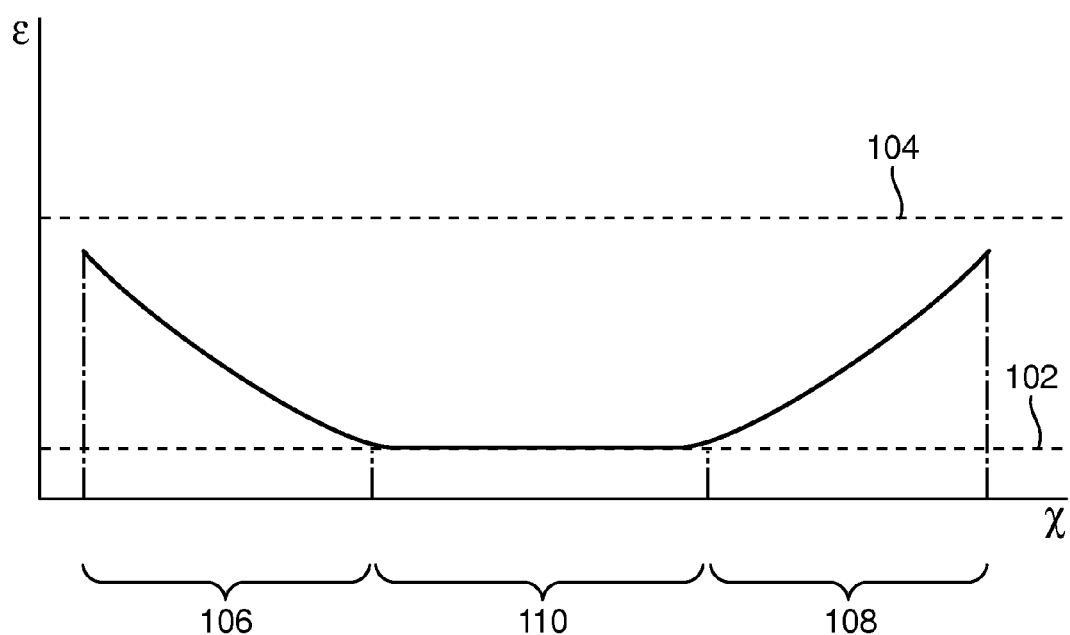
FIG. 6 is graph showing the strain along the length of the repair device, according to one embodiment of the present invention.

With respect to FIG. 6, a graph, strain $\epsilon$ vs. length X, representing the strainability along the length of the repair device 20 under typical tension/load forces that a tendon may place upon the repair device 20 is depicted. In addition, the graph depicts the strainability of prior art devices, such as suture techniques or other prior art devices, represented along reference line 102. Further, the graph depicts the strainability of a native tendon or original tendon that hasn't been damaged, shown along reference line 104. Now with reference to FIGS. 1 and 6, the graph also represents various sections along length X that correspond with various portions along the length 26 of the repair device 20. For example, the graph depicts a first section 106, a second section 108, and a third section 110, which correspond to the first portion 30, the second portion 32, and the intermediate portion 34 of the repair device 20, respectively. The first section 106, corresponding to the first portion 30 of the repair device 20, depicts the strain $\epsilon$ increasing (to the left) along the length 26 of the first portion 30 from the intermediate portion 34 to the first end 46 of the first portion 30. Likewise, the second section 108, corresponding to the second portion 32 of the repair device 20, depicts the strain $\epsilon$ increasing (to the right) along the length 26 of the second portion 32 from the intermediate portion 34 to the second end 48 of the second portion 32. The third section 110, which corresponds to the intermediate portion 34 of the repair device 30, depicts minimized strainability and a substantially constant strain $\epsilon$. As depicted, the first and second portions 30, 32 of the repair device 20 include structure to facilitate strainability or elongation along the length 26 of the repair device 20. Such elongation of the first and second portions 30, 32 attached to a tendon 10 facilitates the tendon to elongate to allow the tendon to function similarly to that of the native tendon while the intermediate portion 34 of the repair device 20 substantially removes the load from the repair site of the lacerated tendon and prevents elongation to facilitate the healing process.

Now referring to FIGS. 7 and 8, another embodiment of a soft tissue repair device 120 is provided. Similar to the previous embodiment, the repair device 120 includes a first portion 122 and a second portion 124 with an intermediate portion 126 therebetween, each portion extending along a longitudinal length 128 of the repair device 120. The first and second portions 122, 124 include structure to facilitate elongation and strainability along the length of the respective first and second portions 122, 124. Also, the intermediate portion 126 may resist strain or elongation its length of the repair device 120. As such, the first and second portions 122, 124 and intermediate portion 126 respond similar to respective first and second sections 106 and 108 and third section in the graph of FIG. 6. Further, as in the previous embodiment, the repair device 120 may include interconnecting struts 130 defining a multi-cellular structure. The struts 130 extending over the length of the first and second portions 122, 124 may be sized and configured to facilitate elongation along the length thereof. Further, the struts 130 extending over the length of the intermediate portion 126 may be sized and configured to substantially resist elongation. The intermediate portion 126 may include laterally extending struts 132. Such laterally extending struts 132 may serve to cage the tendon (not shown) or substantially prevent the end portions of the severed tendon from trumpeting beyond the struts at the intermediate portion 126 of the repair device 120.

In this embodiment, the repair device 120 may primarily be a one piece member and may be cut from a flat sheet of, for example, super-elastic material, such as Nitinol or the like, and then formed into a tubular configuration. In the pre-formed configuration, the repair device 120 may include a peripheral edge 134 with a first end edge 136, a second end edge 138, a first side edge 140 and a second side edge 142. The first and second end edges 136, 138 may include end coupling portions in the form of tabs 144. The tabs 144 may define tab openings 146 sized and configured to couple to end crimps 148. The first and second side edges 140, 142 may also include side coupling portions. Such side coupling portions may include side tabs 150 defining side openings 152. Once the repair device 120 is formed in the tubular configuration, the first side edge 140 may be positioned to abut the second side edge 142 and coupled together via the side openings 152 of the respective first and second side edges 140, 142 to provide a seam 154, shown in outline form in FIG. 8. Such coupling may be employed with crimps, ties, zip-ties, or any other suitable coupling mechanism as known in the art.

Now with reference to FIGS. 7, 7A and 8, one embodiment of an end crimp 148 is provided. The end crimp 148 may include a c-shaped configuration. The end crimp 148 may include an upper end 156 and a lower end 158, each end defining a notch configuration 160 sized and configured to couple to the tab openings 146 defined in the tabs 144 at the first end edge 136 and the second end edge 138 once the repair device 120 has been formed into the tubular configuration. Further, the end crimps 148 may be sized and configured to act as a clamp. As such, once a tendon is positioned within the repair device 120, the end crimps 148 may be sandwiched or, in other words, the upper end 156 and the lower end 158 may be moved closer together to clamp down over the tendon. Such crimping or clamping may minimize potential migration from the repair device when the tendon elongates under a load/tensional force. The end crimps 148 may be a laser cut from a flat sheet of metallic material, such as stainless steel or the like, or any other biocompatible material as known in the art that will substantially maintain a crimped or clamped position.

As previously set forth, the repair device 120 may be formed into a tubular configuration from a flat sheet of, for example, super-elastic material, such as Nitinol. Such may be employed by positioning the flat repair device 120 within or around a jig and heat-setting the repair device 120 in the tubular configuration with the tines 162 oriented substantially orthogonally inward or at an acute angle to extend inward and toward the intermediate portion 126, as known in the art. The tubular configuration may include a cross-section with any appropriate configuration, depending on the particular soft tissue to be repaired. For example, most tendons include an oval cross-section and, as such, the cross-section of the tubular configuration may include a rectangular or oval configuration. However, some tendons include a circular cross-section and, as such, a square or circular configuration may be appropriate. As previously set forth, once heat-set and formed into the desired configuration, the opposing first and second edges may then be coupled together to form the seam 154 and the end crimps 148 may then be assembled to the repair device 120.

With respect to FIGS. 9A, 9B, and 9C, the method steps for employing the repair device 120 with a tendon 10 are provided. For example, FIG. 9A depicts a sectional view of FIG. 9, depicting the repair device 120 in a first position and in its heat-set relaxed state. With respect to FIG. 9B, prior to inserting, for example, a lacerated tendon 10 into the repair device 120, the repair device can be expanded. Such expansion may be employed by inserting an applicator 164 at each end of the repair device 120 to move the repair device 120 to a second position or into an expanded, stressed position. Once expanded, the tubular configuration is broadened or provides a larger cross-sectional opening along the length (not shown) of the repair device 120. Such expanded position efficiently facilitates pulling a first tendon end and a second tendon end with, for example, a suture (not shown), into the repair device 120 while minimizing potentially damaging the tendon on the tines 162. Once the tendon 10 is appropriately positioned within the expanded repair device 120, the applicators 164 may be removed from each end of the repair device 120. The repair device 120 will then automatically move toward its relaxed state or third position and conform around the tendon 10 with the tines 162 engaging the tendon 10, as depicted in FIG. 9C. The end crimps 148, shown in FIG. 8, may then be crimped or clamped to minimize potential migration of the tendon 10 from the repair device 120.

Figure 10:
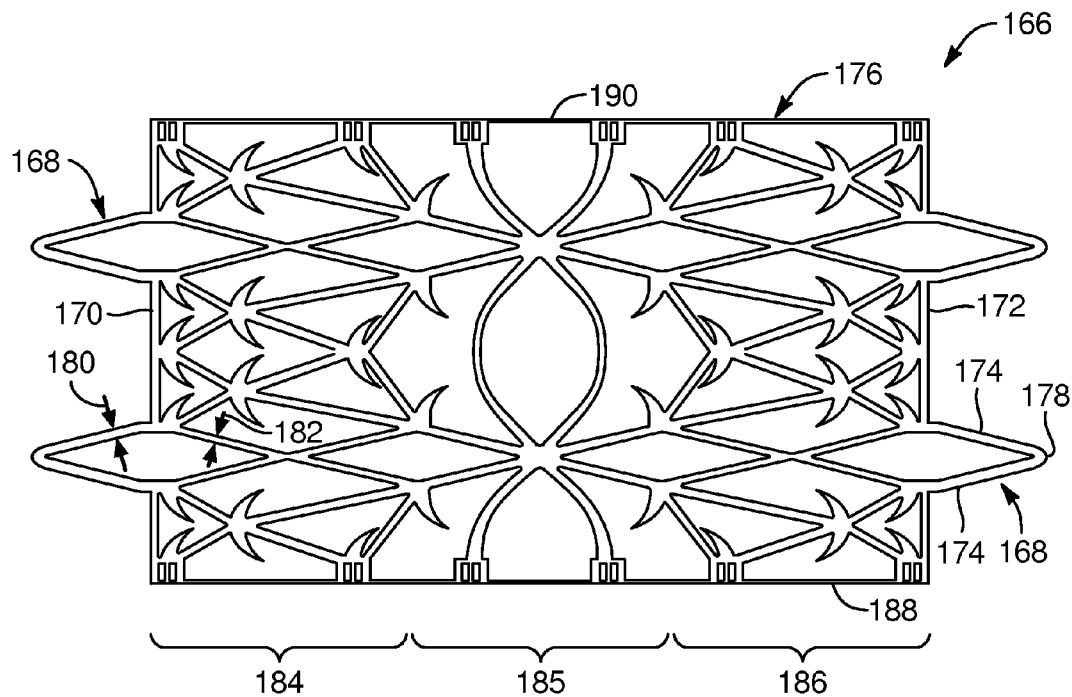
FIG. 10 is a top view of a repair device prior to being formed into a tubular configuration, according to another embodiment of the present invention.
Figure 11:
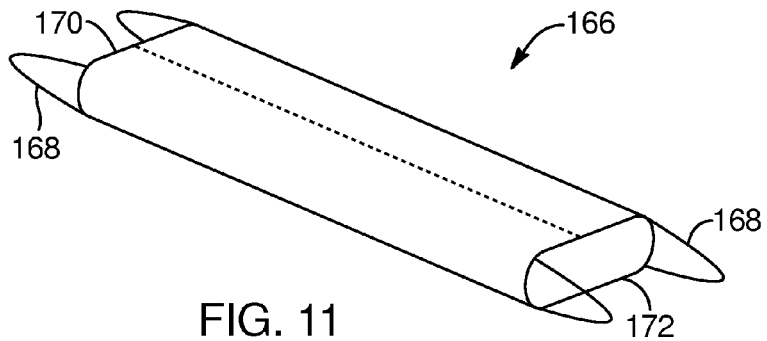
FIG. 11 is a simplistic perspective view of the repair device of FIG. 10, depicting the repair device formed into a tubular configuration with end springs at the ends of the repair device, according to another embodiment of the present invention.

Now with reference to FIGS. 10 and 11, another embodiment of a repair device 166 is provided. This embodiment is similar to the previous embodiment of FIGS. 7 and 8 in most all respects, except instead of end crimps, this embodiment includes spring portions 168. The spring portions 168 may be sized and configured to resist the ends of the repair device 166 widening under stresses the repair device 166 may undergo while also allowing an applicator (not shown) to expand the tubular configuration in preparation for inserting and positioning a tendon within the repair device 166. The spring portions 168 may extend generally from a periphery 176 of the repair device and, more specifically, from a first end edge 170 and a second edge 172 with a v-shaped configuration. Other configurations may also be employed to control stresses within the tubular configuration of the repair device 166. The spring portion 168 may include spring extensions 174 extending from the periphery 176 of the repair device 166 and extend to a common portion 178 to form the v-shaped configuration. The spring extensions 174 may include an extension width 180 that is greater than a width 182 of the struts 183 of the first portion 184 and the second portion 186 of the repair device 166. Struts 183 in the intermediate portion 185 may be similarly sized or may be greater than the width 182 of the struts 183 of the first and second portions 184, 186. With this arrangement, the repair device 166 may be formed from a single piece of, for example, super-elastic material, except for any potential side crimps for coupling the first and second side edges 188, 190 to form the repair device 166 in the tubular configuration. Further, as in the previous embodiments, an important aspect of the present invention is that the first and second portions 184, 186 may elongate along the length of the repair device 166 and respond with a stainability characteristic similar to that shown in respective first and second sections of the graph of FIG. 6. Likewise, the intermediate portion 185 structurally minimizes strainablity and elongation along the length of the repair device 166 to respond similar to the third section of the graph of FIG. 6.

Figure 12:
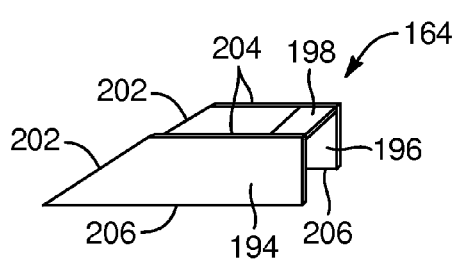
FIG. 12 is a perspective view of an adapter, according to an embodiment of the present invention.

FIG. 12 depicts one embodiment of the before mentioned applicator 164 that may be employed with either of the embodiments shown in FIGS. 8 and 11. With respect to FIGS. 8, 11, and 12, the applicator 164 may include a first side rail 194 and a second side rail 196 with a bridge portion 198 therebetween for joining the first and second side rails 194, 196. Each of the first and second side rails 194, 196 may include a tapered portion 202 to assist in the insertion of the applicator 164 in the tubular configuration of the repair device 120, 166. The first and second side rails 194, 196 each also include an upper edge 204 and lower edge 206. Upon inserting the applicator 164 into the tubular configuration, the tapered portion 202 assists in expanding the tubular configuration to expand the repair device 120 over the upper edge 204 and lower edge 206 of the applicator 164, as depicted in FIG. 9B.

Figure 13:
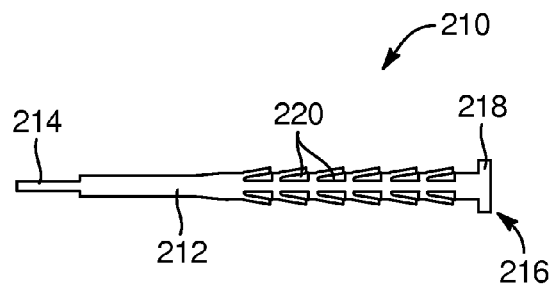
FIG. 13 is a side view of a zip tie, according to another embodiment of the present invention.

FIG. 13 depicts an enlarged view of a zip tie 210. The zip tie 210 is another embodiment that may be employed for coupling ends together at the before mentioned tabs of the repair device. The zip tie 210 may replace the various crimps discussed herein. The zip tie may include an elongated body 212 with a leading end 214 and a trailing end 216 with a back stop 218. The elongated body 212 may include tapered extensions 220 extending therefrom such that the tapered extensions 220 taper towards the leading end 214. The zip tie 210 may be sized and configured such that the leading end 214 can be pulled through the side openings 152 defined in the side tabs 150 of, for example, the tabs 150 of the first and second side edges 140, 142 of the repair device 120 depicted in FIG. 7. Once pulled through the side openings 152 and tightened to a desired position, the excess portion of the zip tie 210 may then be trimmed.

In another embodiment, in addition to, or instead of, the before-mentioned crimps or zip tie, sutures or a wire (not shown), such as a Nitinol wire may be employed to maintain the repair device in the engaging position or second position. For example, in the embodiment shown in FIGS. 1 through 4, rather than employing the side crimps 70, the upper frame portion 38 and the lower frame portion 40 may be coupled together with a suture or flexible wire in a shoe-lace arrangement such that once the upper and lower frame portions 38, 40 are positioned over the tendon 10 the suture or flexible wire may be synched to move the upper and lower frame portions 38, 40 to the second engaging position, as depicted in FIG. 4. The suture and/or wire may be pre-weaved through the appropriate tabs to move the respective frame portions to the second position or be laced through the tabs during the surgical procedure. Such suture and/or wire may be employed in any of the other embodiments described herein, for example, the suture and/or wire may be employed to replace the end crimps 148 depicted in FIGS. 7A and 8.

With reference to FIGS. 14 and 14A, another embodiment of a repair device 310 is depicted. In this embodiment, the repair device 310 includes a first portion 312, a second portion 314 and an intermediate portion 316 therebetween that define a bore 318 and an axis 320 extending through the repair device 310 and along a longitudinal length 324 of the repair device 310. The first and second portions 312, 314 may be referenced as moveable or elongateable portions and the intermediate portion 316 may be referenced as a stabilizing portion sized and configured to resist elongation. In other words, the first and second portions 312, 314 may be configured to move and elongate as a load is placed on the tendon while the intermediate portion 316 may be configured to stabilize tendon ends to be abutted and maintained against each other in a substantially fixed position such that the intermediate portion is also in a substantially fixed position relative to the tendon ends and resists elongation along a length of the intermediate portion. Further, in this embodiment, the first portion 312 and the second portion 314 are two separate tubular frame structures connected with one or more wires 322 interlaced through apertures (not shown) defined at ends the first portion 312 and second portion 314 of the repair device 310, the one or more wires 322 defined as the intermediate portion 316. As will be discussed in further detail below, the longitudinal length 324 of the repair device 310 may be minimized upon application of the repair device 310 to a first tendon portion and a second tendon portion (not shown) such that the intermediate portion 316 will be tightened over lacerated ends of the tendon and minimized along its length.

The first and second portions 312, 314 of the repair device 310 may be laser cut from, for example, a metallic material, such as stainless steel or a super-elastic material. For example, in one embodiment, the repair device may be cut from a flat sheet or tube of super-elastic material, such as Nitinol or the like. In the example of the super elastic material, once laser cut, the components of the repair device may undergo various processes, such as electro-polishing and, if necessary, heat-set in, for example, a heated sand bath to a desired position, as known to one of ordinary skill in the art. Further, the wire may be a metallic material, such as Nitinol or stainless steel.

The first portion 312 may include multiple interconnecting struts 326 to define a multi-cellular structure. The interconnecting struts 326 may extend from the intermediate portion 316 to a first end 328 of the repair device 310 and extend in a tubular configuration to define a portion of the bore 318 extending therethrough. Likewise, the second portion 314 may include the multiple interconnecting struts 326 to define a multi-cellular frame structure and extend from the intermediate portion 316 to a second end 330 of the repair device 310, extending with a tubular configuration to define a portion of the bore 318 of the repair device 310.

Each of the first portion 312 and the second portion 314 may include tines 332 or hooks extending from nodes 334 or junction points of the interconnecting struts 326. The nodes 334 or a node may be defined as the junction of one strut 326 interconnecting to one or more adjacent struts 326, the tines 332 extending from such nodes 334, similar to that set forth in previous embodiments. The tines 332 may extend inward toward the axis 320 of the repair device 310. In another embodiment, the tines 332, of both the first portion 312 and the second portion 314, may extend inward toward the axis 320 and toward the intermediate portion 316 such that the tines 332 of the first portion 312 are oriented in a first direction and the tines of the second portion 314 are oriented in a second direction, similar to that set forth in previous embodiments. In one embodiment, each node 334 may include one or more tines 332 extending therefrom. In another embodiment, the tines 332 may extend from nodes 334 along an upper portion 336 and a lower portion 338 of the repair device 310.

Now with reference to FIGS. 15 through 18, the steps for applying and securing the repair device 310 to a lacerated tendon will now be described. With respect to FIG. 15, the repair device 310 may be removed from sterile packaging (not shown) along with, for example, two needle point suture loops 340, 342 (see FIG. 16). The repair device 310 may be pre-loaded with the first portion 312 over a first applicator 344 and the second portion 314 over a second applicator 346 (see also the description of FIG. 12 of one example of an applicator). Otherwise, the physician may load the first and second portions 312, 314 of the repair device 310 to the first and second applicators 344, 346, respectively. With the repair device 310 positioned over the first and second applicators 344, 346, the repair device 310 is expanded to an orientation or shape that radially enlarges the bore 318 of the repair device 310 to readily facilitate inserting the lacerated tendon into the repair device 310.

Figure 16:
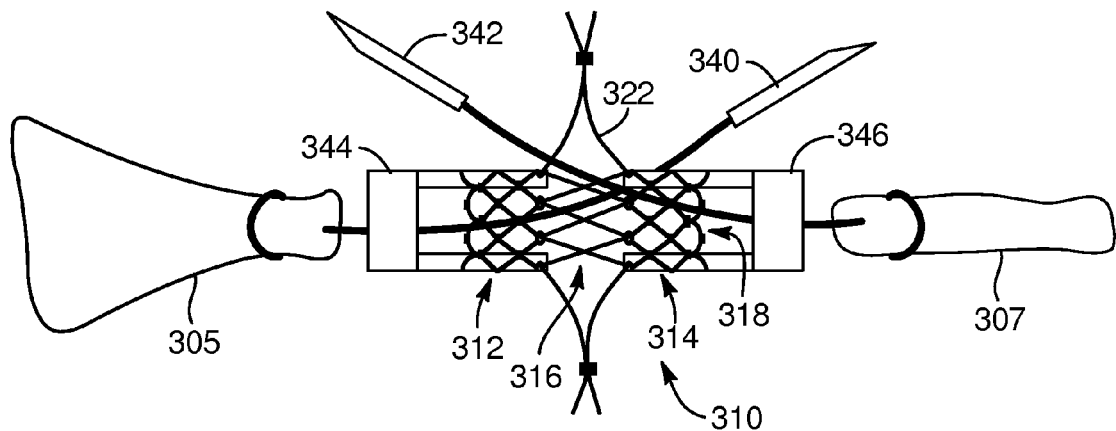
FIG. 16 is a top view of the repair device, depicting the repair device being applied to a lacerated tendon by pulling the tendon ends into the repair device via suture needle loops, according to another embodiment of the present invention.
Figure 17:
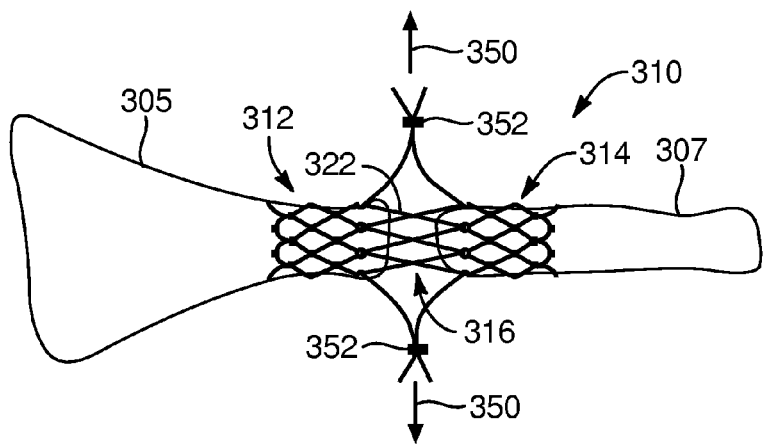
FIG. 17 is a top view of the repair device, depicting the repair device positioned over a lacerated tendon upon the applicators and suture needle loops are removed, according to another embodiment of the present invention.

As depicted in FIGS. 16 and 17, the first and second needle point suture loops 340, 342 may be passed through and secured to the first tendon portion 305 and a second tendon portion 307, respectively, employing suturing techniques as known to one of ordinary skill in the art. The repair device 310 may then be positioned between the first and second tendon portions 305, 307. The first tendon portion 305 may then be pulled through the bore 318 of the first portion 312 of the repair device 310 by pulling the secured first suture loop 340 into the bore so that the end of the first suture loop 340 is passed through the wires 322 of the intermediate portion 316, as depicted. Similarly, the second tendon portion 307 may then be pulled into the bore 318 of the second portion 314 of the repair device 310 via the second suture loop 342. Once the first tendon portion 305 is positioned within the bore 318 of the first portion 312 of the repair device 310, the first applicator 344 can be removed and the first suture loop 340 may be removed or cut from the first tendon portion 305. Likewise, upon the second tendon portion 307 being positioned within the bore 318 of the second portion 314 of the repair device 310, the second applicator 346 and second suture loop 342 may be removed, as depicted in FIG. 17. Upon the first and second applicators 344, 346 being removed from the first and second tendon portions 305, 307, the radial dimension or height of the bore 318 automatically is minimized along a length of the first and second portions 312, 314 of the repair device 310 such that the tines 332 (FIG. 14A) engage the tendon to anchor the repair device thereto.

Figure 18:
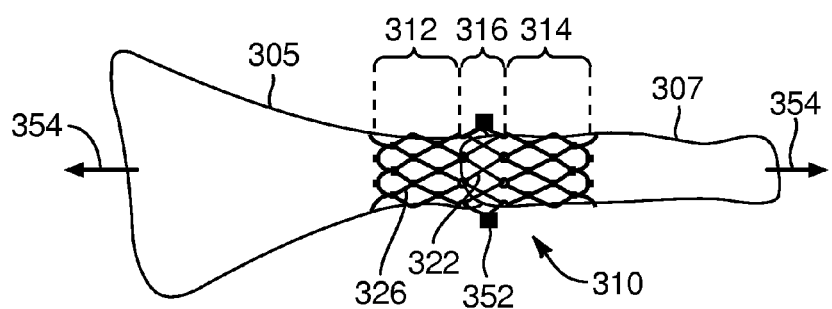
FIG. 18 is a top view of the repair device, depicting an intermediate portion of the repair device synched to abut ends of the lacerated tendon, according to another embodiment of the present invention.

At this juncture, with reference to FIGS. 17 and 18, the one or more wires 322 of the intermediate portion 316 may be pulled by the physician, as indicated by arrows 350, so as to pull the first portion 312 and the second portion 314 closer to each other. Further, such pulling of the one or more wires 322 pulls respective ends of the first and second tendon portions 305, 307 against each other in an abutted arrangement. The one or more wires 322 may include one or more swages 352 or crimps that can be tightened down over the one or more wires 322 to maintain the first and second tendon portions 305, 307 against each other. With this arrangement, the intermediate portion 316 of the repair device 310 substantially maintains the ends of the respective first and second tendon portions 305, 307 in the abutted arrangement while the first portion 312 and the second portion 314 is anchored or harnessed to the lacerated tendon via the tines 332.

With respect to FIGS. 6 and 18, similar to previous embodiments, the multi-cellular frame structure of the first portion 312 and second portion 314 of the repair device 310 may elongate upon a load being placed upon the tendon while the intermediate portion 316 substantially prevents elongation of the ends of the first and second tendon portions 305, 307, maintaining such ends to in the abutted arrangement. For example, similar to previous embodiments, the structural characteristics of the interconnecting struts 326 extending along the first portion 312 and the second portion 314 of the repair device 310 may be sized and configured (e.g., by tapering along their lengths or varying the thickness of the struts or varying the angle of the struts, arcuate portions along lengths of struts (cell configuration), material properties, etc.) to facilitate elongation upon a load being placed upon the tendon. In this manner, the first portion 312 and the second portion 314 may strain or elongate along their respective lengths similar to that depicted in sections 106 and 108, respectively, of the strain-length graph of FIG. 6. Similarly, the intermediate portion 316, made of one or more wires 322 interlaced with the first and second portions 312, 314 of the repair device 310, may be sized and configured to substantially prevent or resist strain or elongation along the intermediate portion 316 of the repair device 310, similar to that depicted in section 110 of the strain vs. length graph of FIG. 6. With this arrangement, the repair device 310 can facilitate elongation of a loaded tendon while also maintaining the lacerated ends of the first and second tendon portions 305, 307 in the abutted arrangement.

Now with reference to FIGS. 19-22, another embodiment of a repair device 410 configured to harness and repair a lacerated tendon 403 is depicted. This embodiment is similar to the previous embodiment in that the repair device 410 includes separate portions coupled together, such as a first part 426 and a second part 427 with one or more wires 418 coupling the first part 426 to the second part 427, except this embodiment may not include integrally formed anchors/tines, but rather, the repair device 410 of this embodiment may employ separate and discrete anchoring components, such as staples 472 (FIG. 22), to anchor the repair device 410 to the tendon 403.

Figure 19:
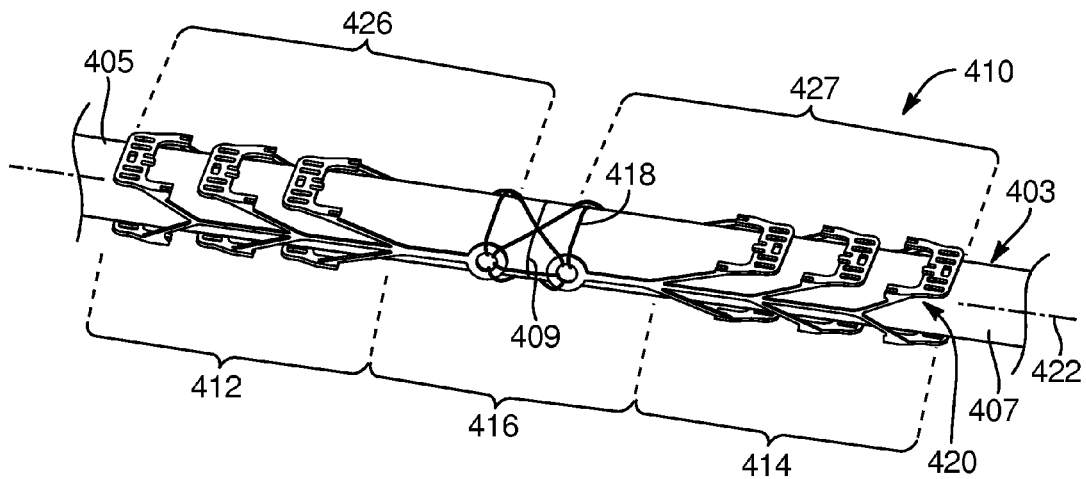
FIG. 19 is a perspective view of another embodiment of a repair device, depicting the repair device coupled to a lacerated tendon, according to the present invention.

With respect to FIG. 19, the repair device 410 may include a first portion 412, a second portion 414 and an intermediate portion 416 extending between the first and second portions 412, 414, the intermediate portion 416 including, among other portions, the one or more wires 418. As in the previous embodiments, the first and second portions 412, 414 may be referenced as moveable or elongateable portions and the intermediate portion 416 may be referenced as a stabilizing portion that is sized and configured to resist elongation. In other words, the first and second portions 412, 414 may be configured to move and elongate (or even move to an arcuate position) as a load is placed on the tendon while the intermediate portion 416 may be configured to stabilize tendon ends to be abutted and maintained against each other in a substantially fixed position with the intermediate portion 416 also in a substantially fixed position relative to the tendon ends such that the intermediate portion 416 resists elongation along a length of the intermediate portion.

Further, the first part 426 may define the first portion 412 and a portion of the intermediate portion 416. Similarly, the second part 427 may define the second portion 414 and another portion of the intermediate portion 416. The first portion 412 and the second portion 414 may be sized and configured to be positioned over a first tendon portion 405 and a second tendon portion 407, respectively, and the intermediate portion 416 of the repair device 410 may be configured to span and be positioned over abutted ends 409 and end portions of the lacerated tendon 403. As in previous embodiment, the repair device 410 may define a bore 420 and an axis 422 each extending longitudinally through the repair device 410 to receive the lacerated tendon 403. With this arrangement, the repair device 410 may act as a harness type structure for a lacerated tendon 403 with first and second portions 412, 414 that dynamically move relative to the variable loads and movement made by the tendon and with the intermediate portion 416 controlling and minimizing movement of the abutted ends 409 of the lacerated tendon 403.

The structure of the repair device 410 may include various struts, extensions, and/or portions, some of which may define a multi-cellular structure, each having a particular function described in detail herein. Further, the first part 426 and the second part 427 of the repair device 410 may be laser cut from, for example, a tube of super-elastic material, such as Nitinol. As such, the first and second parts 426, 427 of the repair device 410 may each be its own unitary and monolithic structure having been made from a single piece of tube. Once laser cut, the first and second parts 426, 427 of the repair device 410 may undergo various processes, such as electro-polishing and, if necessary, heat-set in, for example, a sand bath to a desired position, as known to one of ordinary skill in the art. The one or more wires 418 may be metallic, such as Nitinol or stainless steel, or any other suitable and biocompatible material. In another embodiment, the first and second parts 426, 427 of the repair device may not be separated as two components, but rather, formed from a single tube of material and formed as a unitary, seamless, monolithic structure With respect to FIGS. 20 and 21, for simplification purposes, only the first part 426 defining the first portion 412 and a first intermediate portion 424 of the repair device 410 is depicted, although the second part 427 (FIG. 19) may be a mirror image of the first part 426 and may be substantially similar in functionality, parts, and portions in all respects.

The first part 426 of the repair device 410 may include a first side 428, a second side 430, an upper side 432 and a lower side 434 defining the axis 422 and the bore 420 extending axially therethrough and extending between a first end 436 and a second end 438 of the first part 426. The first side 428 and the second side 430 may each include a tree-like structure having a trunk 440 and multiple branches 442. Each trunk 440 of the first part 426 of the repair device 410 may define the first intermediate portion 424. Further, each trunk 440 may include a width 444 that is larger than a branch width 446. Each trunk 440 may extend between the second end 430 and the branches 442 or, otherwise referred to, the first portion 412 of the repair device 410, the second end 438 of the first part 426 defining an eyelet 448 for lacing the before-mentioned one or more wires 418 (FIG. 19). Further, the trunk 440 may be proportionately smaller or larger in length relative to the first portion 412 than that which is depicted.

As previously set forth, each of the first and second sides 428, 430 may include the trunk 440 with multiple branches 442, each extending with a substantially similar profile and pattern. For example, the branches 442 may include a first branch set 450, a second branch set 452 and a third branch set 454, each extending from a junction point 456. The first branch set 450 may extend directly from the trunk 440 or the junction point 456 between the trunk 440 and the first branch set 450. The first branch set 450 may include an upper branch 442*a*, a middle branch 442*b* and a lower branch 442*c*. The upper branch 442*a* may extend at an angle relative to the middle branch 442*b*, extending upward and toward the first end 436 of the first part 426 of the repair device 410. The lower branch 442*c* may extend at a similar angle, but a mirror image of the upper branch 442*a*, extending downward and toward the first end 436 of the first part 426 of the repair device 410. The middle branch 442*b* may extend toward the first end 436 and parallel with the axis 422 of the repair device 410. Further, the middle branch 442*b* of the first branch set 450 may extend toward the junction point 456 of the second branch set 452. The first branch set 450 and the second branch set 452 may extend similar to each other, the second branch set 452 including the middle branch 442*b* that extends to the third branch set 454. In one embodiment, the third branch set 454 may include the upper branch 442*a* and the lower branch 442*c*, without the middle branch 442*b*. In another embodiment, the third branch set 454 may include the middle branch 442*b* that extends to a fourth branch set (not shown). This may be repeated with additional branch sets depending on the desired extending branch sets for a given length of the first part 426 of the repair device 410.

As previously set forth, each of the first side 428 and second side 430 of the first part 426 of the repair device 410 may extend similarly to each other with respective trunks 440 and branches 442. With that stated, the first side 428 and the second side 430 may be coupled to each other with lateral extensions 458 or pad portions extending between respective upper branches 442*a* and lower branches 442*c* of each of the branch sets. For example, the upper branch 442 of the first branch set 450 on each of the first side 428 and the second side 430 of the first part 426 of the repair device 410 may extend to one lateral extension 458 or, more specifically, an upper pad portion 460. Likewise, the lower branch 442*c* of the first branch set 450 on each of the first side 428 and second side 430 of the repair device 410 may extend to another lateral extension 458 or a lower pad portion 462. Each branch set may similarly extend with its upper branch 442*a* and lower branch 442*c* to an upper pad portion 460 and a lower pad portion 462, respectively. The upper and lower pad portions 460, 462 may at least partially define the upper side 432 and the lower side 434 of the first part 426 of the repair device 410. Each pad portion may include an inner surface 464 and an outer surface 466, the inner surface 464 facing the axis 422 of the repair device 410. Further, the upper pad portion 460 may directly face the lower pad portion 462. For example, the upper branch 442*a* of the first branch set 450 extends to the upper pad portion 460 and the lower branch 442*c* of the first branch set 450 extends to the lower pad portion 462 such that the inner surfaces 464 of the upper pad portion 460 and the lower pad portion 462 correspond and face each other. The upper and lower pad portions 460, 462 of the second and third branch sets 452, 454 may be similarly arranged. In addition, the outer surfaces 466 of the upper and lower pad portions 460, 462 may face directly away from each other. The inner and outer surfaces 464, 466 of each of the pad portions may be substantially planar. In one embodiment, the inner and/or outer surfaces 464, 466 may include one or more atraumatic tabs that may protrude from the surfaces for aligning purposes.

Each of the upper and lower pad portions 460, 462 may include one or more through holes 468 and one or more indents 470 in the form of a notch extending through a portion of the pad. For example, each pad portion may define two pair of holes 468 extending through the pad portion such that the holes 468 of the upper pad portion 460 correspond and are aligned with the holes 468 of the corresponding lower pad portion 462. Further, the outer surface 466 (or the inner surface) of each of the pad portions may include the indents 470 or atraumatic tabs sized and configured to align each upper pad portion 460 with its corresponding lower pad portion 462 when expanded with, for example, an applicator (not shown). In the case of employing indents 470 for aligning purposes, the applicator may include tabs that may fit and align within the indents 470 to properly align the device within the applicator. In the case of tabs, the applicator may have corresponding tabs or indents to facilitate proper alignment of the repair device within the applicator. Further description of the holes 468 and indents 470 or notches will be provided hereafter.

Figure 20:
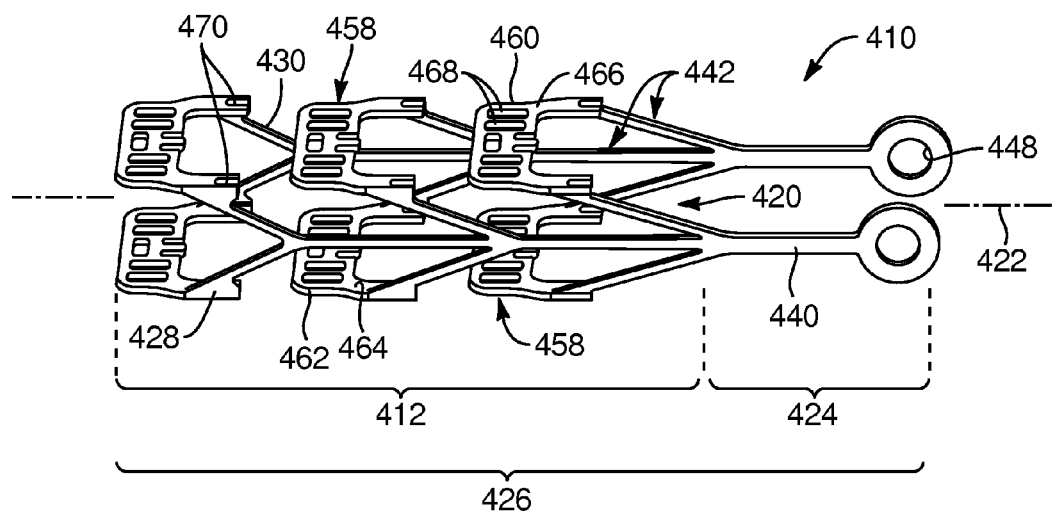
FIG. 20 is a perspective view of a first part of the repair device of FIG. 19, depicting the repair device in a non-strained position, according to another embodiment of the present invention.
Figure 21:
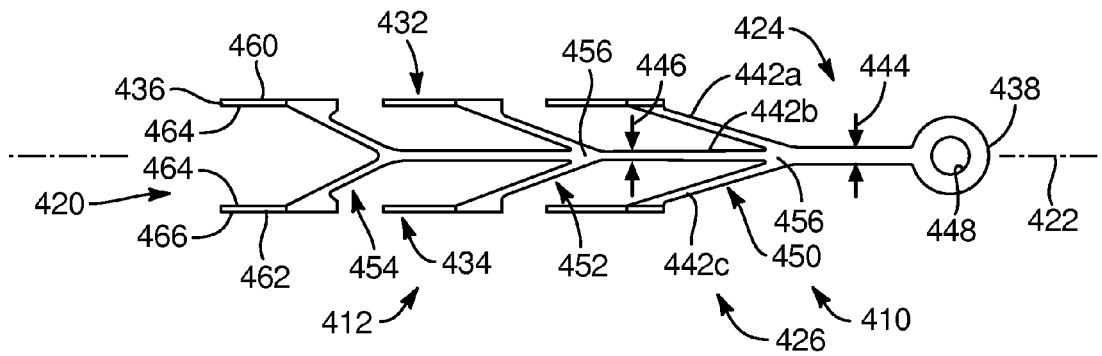
FIG. 21 is a side view of the first part of the repair device, depicting a side profile of the first part of the repair device, according to another embodiment of the present invention.
Figure 22:
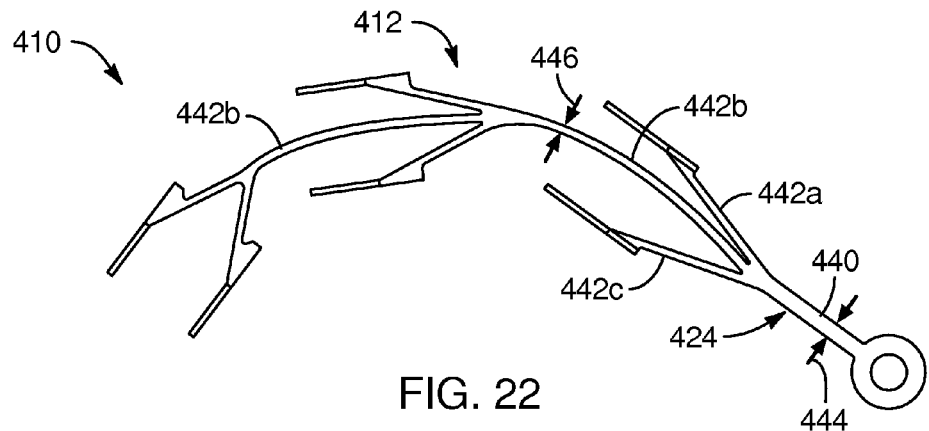
FIG. 22 is a side view of the first part of the repair device, depicting the first part of the repair device moved to an arcuate position, according to another embodiment of the present invention.

With respect to FIGS. 20 and 22, as previously set forth, the first intermediate portion 424 or trunk 440 includes a width 444 greater than the branch width 446 of each middle branch 442*b* and may also be greater than a width of each upper and lower branches 442*a*, 442*c*. The width 444 of the trunk 440 may be sized and configured to stabilize the ends of the lacerated tendon 403 (see FIG. 19). Further, such width 444 may be sized to minimize bending of the trunk so that movement of a portion of the tendon 403 situated along the first intermediate portion 424 is also minimized. With that being said, the middle branches 442*b* extending along the first portion 412 of the repair device 410 may be sized and configured to facilitate bending or to facilitate the first portion 412 of the repair device 410 to be moveable to an arcuate position or moveable with a tight radial turn, such as up to a 90 degree angle. Such bending may be useful depending on the type of tendon 403 being repaired, such as a digit tendon along one's finger. Further, the upper and lower branches 442*a*, 442*c* of each branch set may be sized and configured to bend and correspond with the arcuate position of the middle branch 442*b*. Further, the upper and lower branches 442*a*, 442*c* of each branch set may be sized and configured to facilitate elongation of the first portion 412 as a load is placed upon the tendon 403 to which the first portion 412 is attached and the tendon naturally wants to elongate and/or move along a bend. As in previous embodiments, as the first portion 412 elongates and facilitates elongation of the tendon 403, the intermediate portion 416 or first intermediate portion 424 substantially prevents elongation to minimize movement at the ends of the lacerated tendon 403. Further, as in previous embodiments, the first portion 412 may elongate with a strain gradient similar to that shown in the corresponding section 106 of FIG. 6. Similarly, the intermediate portion 416 of the repair device 410 may be sized and configured to substantially prevent or resist strain and elongation along that portion of the repair device 410 similar to that shown in section 110 of FIG. 6 and, therefore, substantially prevents separation of the ends of the lacerated tendon 403. As set forth previously, the first part 426 of repair device 410 is a mirror image of a second part 427 of the repair device 410, as depicted in FIG. 19 and, therefore, may structurally behave in a similar manner.

Figure 23:
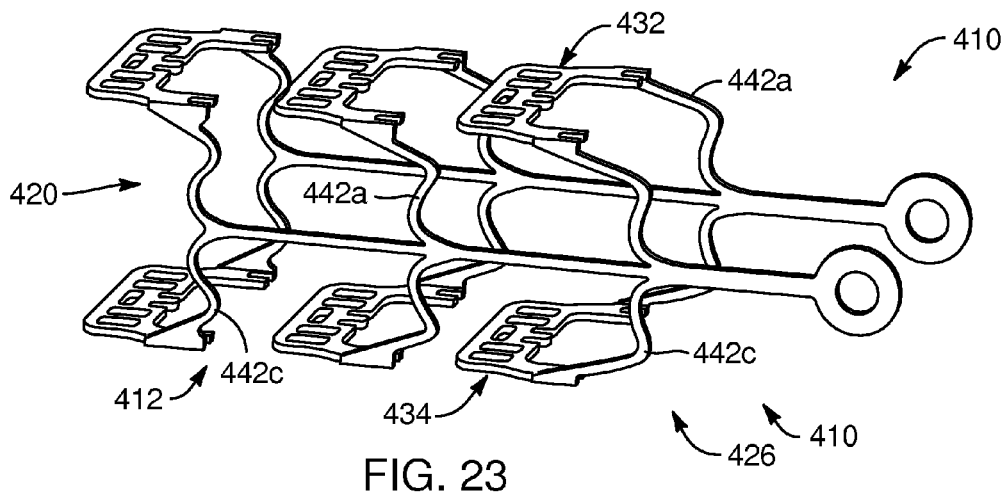
FIG. 23 is a perspective view of the first part of the repair device, depicting the repair device in a strained position as if loaded in an applicator, according to another embodiment of the present invention.

With respect to FIG. 23, the first part 426 of the repair device 410 is depicted in a strained position. It is noted that the second part (not shown) of the repair device 410 may be similarly moved to the strained position. The first part 426 of the repair device 410 may be moved to the strained position with an applicator (not shown) similar to that provided in previous embodiments. In the strained position, the upper and lower branches 442a, 442c of each branch set may be moved to extend upward and downward, respectively, toward the respective upper side 432 and lower side 434 of the repair device 410. In this manner, the bore 420 extending through the first portion 412 of the repair device 410 may be enlarged to readily facilitate pulling a first tendon portion (not shown) through the bore 420, similar to that depicted in the previous embodiment.

Figure 24:
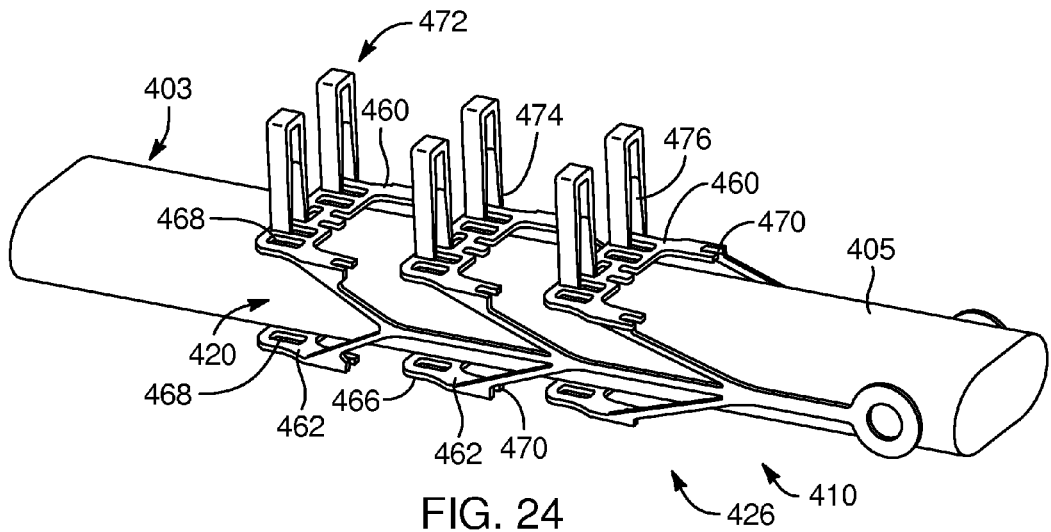
FIG. 24 is perspective view of the first part of the repair device, depicting the repair device positioned over a first tendon portion of a lacerated tendon and staples in a non-stapled position, according to another embodiment of the present invention.

With reference to FIG. 24, the first part 426 of the repair device 410 positioned over the first tendon portion 405 is depicted with staples 472 in a non-stapled position. Once the first tendon portion 405 is pulled through the bore 420 of the first part 426 of the repair device 410, the repair device 410 may be anchored to the lacerated tendon 403 with, for example, staples 472. The staples 472 may be applied via an applicator (not shown) with a staple cartridge (not shown) that may be integrated with the applicator. The staples 472 are depicted in a non-stapled position as if positioned in the staple cartridge. In the non-stapled position, the staples 472 may be disposed directly over the holes 468 defined in each of the upper pad portions 460. The staples 472 may include an elongated u-shaped configuration with free ends 474 and legs 476. The staples 472 may be properly aligned with the holes 468 with indents 470 or notches defined in the upper and lower pad portions 460, 462 such that the applicator/staple cartridge may include corresponding structure, such as tabs to ensure proper alignment of the repair device 410.

To anchor the repair device 410 to the lacerated tendon 403, the staple cartridge may be compressed so that the free ends 474 pass through the holes 468 in the upper pad portions 460 and continue downward, passing through the tendon 403 and through corresponding holes 468 in the lower pad portion 462. The free ends 474 may fold over along the outer surface 466 of the lower pad portions 462. With this arrangement, the repair device 410 may be coupled to the lacerated tendon 403. Once the staples 472 are in the stapled position to anchor the repair device 410 to the tendon 403, the applicator/staple cartridge (not shown) may be removed and the one or more wires 418 (FIG. 19) may be synched over the ends of the lacerated tendon 403 and held tight with swages or crimps (not shown), similar to that described and depicted in FIGS. 17 and 18 of the previous embodiment. In this manner, the repair device 410 may be anchored to the lacerated tendon 403 by employing separate and discrete components relative to the repair device, such as the staples 472.

In another embodiment, the repair device 410 may include tines extending from the inner surface 464 of the upper and lower pad portions 460, 462 of the repair device 410 to act in conjunction with the staples 472 to anchor or harness the repair device 410 to the lacerated tendon 403. In another embodiment, the repair device 410 may include tines or hooks (without the use of staples) for anchoring or harnessing the repair device 410 to the lacerated tendon 403. Further, in another embodiment, the first part 426 and the second part 427 of the repair device 410 may be formed as a single monolithic structure from a single tube, similar to that described in previous embodiments. It is also contemplated that the present invention of providing a moveable portion of the repair device to be moveable with tissue while another portion of the repair device is substantially fixed adjacent a repair site to facilitate proper healing at the repair site, but also providing the mobility for optimal tissue healing may also be applied to other structures in the body, such as tissue-to-bone and bone-to-bone structures. Such a device may include a tubular structure, a partially tubular structure, and/or a plate like structure including multiple interconnecting struts that may define a multi-cellular structure.

Other examples of soft tissue repair devices, methods, and systems are set forth in U.S. patent application Ser. No. 12/783,507, filed on May 19, 2010, entitled TISSUE FIXATION, and U.S. patent application Ser. No. 13/021,653, filed on Feb. 4, 2011, entitled TISSUE STABILIZATION SYSTEM, and U.S. patent application Ser. No. 13/021,651, filed Feb. 4, 2011, entitled SYSTEM FOR TISSUE FIXATION TO BONE, the disclosures of which are incorporated by reference herein in their entirety.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A soft tissue repair device configured to fuse a first tendon end and a second tendon end of a lacerated tendon together, the repair device comprising:

a frame having a tubular structure and defining an axis and a bore, the frame including multiple struts interconnected and extending with a monolithic structure to at least partially define the tubular structure, the frame configured to receive the first tendon end and the second tendon end, the frame including a first portion and a second portion with an intermediate portion therebetween, the first portion and the second portion including anchors extending directly therefrom and into the bore and configured to attach the frame to portions of the tendon, the intermediate portion configured to be positioned adjacent the first and second tendon ends to substantially maintain the first tendon end to abut the second tendon end, the intermediate portion being configured to substantially resist elongation so as to maintain a substantially fixed position relative to the first and second tendon ends, the first portion and the second portion configured to be positioned over and attach to separate portions of the tendon, the frame configured to elongate along a length of the respective first portion and the second portion of the frame as the portions of the tendon elongate.

2. The soft tissue repair device of claim 1, wherein the frame comprises pad portions defining holes therethrough, the pad portions configured to receive the anchors through the holes to secure the frame to the tendon.

3. The soft tissue repair device of claim 1, wherein the anchors comprise at least one of tines and staples.

4. The soft tissue repair device of claim 1, wherein the intermediate portion comprises a wire connecting the first portion and the second portion of the frame together.

5. The soft tissue repair device of claim 1, wherein struts of the first portion and the second portion of the frame are moveable to an arcuate position.

6. The soft tissue repair device of claim 1, wherein the struts of the first portion and the second portion of the frame are moveable to an arcuate position with the struts of the intermediate portion substantially maintaining the fixed position.

7. The soft tissue repair device of claim 1, wherein the frame is configured to substantially maintain the fixed position along a length of the intermediate portion of the frame.

8. The soft tissue repair device of claim 1, wherein the struts of the first portion and the second portion comprise a multi-cellular structure.

9. The soft tissue repair device of claim 1, wherein the frame comprises a first side, a second side, an upper side and a lower side, the first side being opposite the second side, the first and second sides including the struts to at least partially define the first and second sides, the struts extending to multiple pad portions to at least partially define the upper and lower sides of the frame, each pad portion along the upper side being directly opposite and facing another pad portion along the lower side of the frame.

10. The soft tissue repair device of claim 9, wherein the pad portions comprise holes extending therethrough configured to receive the anchors for securing the first portion and the second portion of the frame to the tendon.

11. A repair device configured to fuse tissue at a repair site, the repair device comprising:
a frame having multiple struts interconnected and extending with a monolithic structure and configured to extend along opposing sides of the tissue, the frame including a moveable portion and a stabilizing portion, the moveable portion coupled to the stabilizing portion, the moveable portion of the frame extending with at least opposite first and second sides configured to be positioned over opposite sides of the tissue such that the frame defines an axis, the stabilizing portion of the frame extending adjacent the repair site and the moveable portion of the frame configured to be anchored to a portion of the tissue separate from the repair site; and
anchors configured to extend inward from the moveable portion of the frame and between the first and second sides of the frame;
wherein the moveable portion of the frame is moveable to elongate along a length of the moveable portion of the frame as the portion of tissue elongates with a load placed thereon; and
wherein the stabilizing portion of the frame maintains a substantially fixed position adjacent the repair site.

12. The repair device of claim 11, wherein the moveable portion of the frame comprises pad portions defining holes therethrough, the pad portions configured to receive the anchors through the holes to secure the frame to the tendon.

13. The repair device of claim 11, wherein the anchors comprise at least one of tines and staples.

14. The repair device of claim 11, wherein the stabilizing portion comprises a wire.

15. The repair device of claim 11, wherein the moveable portion of the frame is moveable to an arcuate position.

16. The repair device of claim 11, wherein the struts of the frame comprise a multi-cellular structure.

17. The repair device of claim 11, wherein the moveable portion of the frame is moveable to an arcuate position as the portion of tissue to which the moveable portion is anchored moves to an arcuate position.

18. The soft tissue repair device of claim 1, wherein the struts of the intermediate portion extend substantially parallel relative to the axis of the frame.

19. The repair device of claim 11, wherein the struts of the stabilizing portion extend substantially parallel relative to the axis of the frame.

* * * * *